US012260937B2

(12) United States Patent
Yekhanin et al.

(10) Patent No.: US 12,260,937 B2
(45) Date of Patent: Mar. 25, 2025

(54) REVERSE CONCATENATION OF ERROR-CORRECTING CODES IN DNA DATA STORAGE

(71) Applicant: Microsoft Technology Licensing, LLC, Redmond, WA (US)

(72) Inventors: Sergey Yekhanin, Redmond, WA (US); Sivakanth Gopi, Redmond, WA (US); Henry Pfister, Durham, NC (US); Karin Strauss, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1244 days.

(21) Appl. No.: 16/562,183

(22) Filed: Sep. 5, 2019

(65) Prior Publication Data

US 2021/0074380 A1    Mar. 11, 2021

(51) Int. Cl.
*G16B 30/10*   (2019.01)
*G06F 11/08*   (2006.01)
*G06F 16/903*  (2019.01)

(52) U.S. Cl.
CPC ............ *G16B 30/10* (2019.02); *G06F 11/085* (2013.01); *G06F 16/90344* (2019.01)

(58) Field of Classification Search
CPC ....... G16B 30/10; G16B 50/00; G06F 11/085; G06F 16/90344; G11C 13/0019
See application file for complete search history.

(56) References Cited

U.S. PATENT DOCUMENTS

| | | |
|---|---|---|
| 9,898,579 B2 | 2/2018 | Strauss et al. |
| 2017/0141793 A1 | 5/2017 | Strauss et al. |
| 2018/0211001 A1 | 7/2018 | Gopalan et al. |
| 2018/0223340 A1 | 8/2018 | Chen et al. |
| 2018/0223341 A1 | 8/2018 | Chen et al. |
| 2018/0230509 A1 | 8/2018 | Chen et al. |
| 2018/0253528 A1 | 9/2018 | Strauss et al. |
| 2018/0265921 A1 | 9/2018 | Chen et al. |
| 2019/0258909 A1 | 8/2019 | Church |

FOREIGN PATENT DOCUMENTS

| | | |
|---|---|---|
| WO | WO 2018148260 | 8/2018 |
| WO | WO 2019020059 | 1/2019 |

OTHER PUBLICATIONS

Mittelholzer T & Eleftheriou E. Reverse concatenation of production and modulation codes. IEEE Communications Proceedings of 2008, 10.1109/ICC.2008.382. (Year: 2008).*
Vamos P. Adaptive constrained coding. PhD Thesis, Budapest University of Technology and Economics. (Year: 2013).*
Grass RN, Heckel R, Puddu M, Paunescu D, Stark WJ. Robust chemical preservation of digital information on DNA in silica with error-correcting codes. Angewandte Chemi International Edition 54: 2552-2555 (Year: 2015).*
Schouhamer Immink KA. IEEE Communications Letters 22(2): 224-227. (Year: 2018).*
Krishnan AR. Barcodes for DNA sequencing with guaranteed error correction capability. Electronics Letters 47(4): 1-2. (Year: 2011).*
Yazdi SMHT. Portable and error-free DNA-based data storage. Scientific Reports 7(5011): (Year: 2017).*
"Reed-Solomon error correction," *Wikipedia*, wikipedia.org, visited Jul. 29, 2019, 20 pages.
"Low-density parity-check code," *Wikipedia*, wikipedia.org, visited Jul. 29, 2019, 8 pages.
"Luby transform code," *Wikipedia*, wikipedia.org, visited Jul. 29, 2019, 4 pages.
"Hamming code," *Wikipedia*, wikipedia.org, visited Jul. 29, 2019, 7 pages.
Arikan, "An implementation of Elias coding for input-restricted channels," IEEE Transactions on Information Theory, vol. 36, No. 1, Jan. 1990, 4 pages.
McWilliams, F.J., Sloane, N.J.A., The Theory of Error-Correcting Codes, 1977, 771 pages [submitted in four parts].
Levenshtein, "Binary codes capable of correcting deletions, insertions, and reversals," Soviet physics doklady, 1966, 4 pages.
Tenengolts, "Nonbinary codes, correcting single deletion or insertion," IEEE Transactions on Information Theory, vol. 30, No. 5, Sep. 1984, 4 pages.
Bliss, "Circuitry for performing error correction calculations on basedband encoded data to eliminate error propagation," IBM Tech. Discl. Bull., vol. 23, pp. 4633-4634, Mar. 1981.
Mittelhozler et al., "Reverse concatenation of product and modulation codes," Proc. of ICC 2008, 6 pages.
Grass et al., "Robust chemical preservation of digital information on DNA in silica with error-correcting codes," Angew. Chem. Int. Ed. 54, 2552-2555 (2015).
Blawat, M., et al. "Forward error correction for DNA data storage," Procedia Comput. Sci. 80, 1011-1022 (2016).
Erlich, Y., Zielinski, D. "Dna Fountain enables a robust and efficient storage architecture," Science 355, 950-954 (2017).
Organick, et al. "Random access in large scale DNA data storage," *Nat. Biotechnol.* 36, 242-248, Feb. 19, 2018, 9 pages.

(Continued)

*Primary Examiner* — Olivia M. Wise
*Assistant Examiner* — Robert J. Kallal
(74) *Attorney, Agent, or Firm* — Klarquist Sparkman, LLP

(57) ABSTRACT

Redundancy information can be included in nucleotide symbol strings encoding underlying data. To avoid propagation of errors during the decoding process, during encoding, a constrained encoding can be performed before the redundancy information is computed. The redundancy information can be an outer encoding across multiple nucleotide symbol strings. An inner coding within nucleotide symbol strings can also be supported. Such redundancy information can be interleaved into the underlying nucleotide symbol strings to which the constrained encoding has been applied, resulting in a relaxed constraint. Insertion/deletion redundancy information can also be included in the resulting strings, and an insertion/deletion-sensitive sequence can be included to assist in recovering accurate sequences during decoding operations.

19 Claims, 24 Drawing Sheets

(56) References Cited

OTHER PUBLICATIONS

International Search Report and Written Opinion received in PCT Application No. PCT/US2020/037995, mailed Sep. 2, 2020, 11 pages.
Cideciyan et al., "Partial Reverse Concatenation for Data Storage," *Signal and Information Processing Association Annual Summit and Conference* (APSIPA), 2014 Asia-Pacific, DOI: 10.1109/APSIPA. 2014.7041670, 2014, 9 pages.
Marcus et al., *An Introduction to Coding for Constrained Systems*, Fifth Edition (Oct. 2001), 289 pages.
Gabrys et al., "Segmented Reverse Concatenation: A New Approach to Constrained ECC," IEICE, ISITA 2020, Kapolei, Hawai'i, USA, Oct. 24-27, 2020, 5 pages.

\* cited by examiner

| MAX HOMOPOLY. RUN LENGTH | SPACING | GROUP SIZE | MAX FINAL HOMOPOLY. RL | CODE REDUNDANCY |
|---|---|---|---|---|
| 1 | 4 | 1 | 2 | 25% |
| 3 | 4 | 1 | 4 | 25% |
| 3 | 3 | 1 | 5 | 33% |
| 1 | 1 | 2 | 5 | 200% |
| 1 | 2 | 3 | 4 | 150% |

1300

SOFTWARE 2380 IMPLEMENTING TECHNOLOGIES

US 12,260,937 B2

REVERSE CONCATENATION OF ERROR-CORRECTING CODES IN DNA DATA STORAGE

FIELD

The field generally relates to error-correcting codes in DNA data storage.

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding that string, sequenced the synthetic DNA, and then recovered the original computer file with 100% accuracy.

However, while amazing strides have been made in the field, there still remains room for improvement, particularly in how errors are addressed by the encoding and decoding processes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a method comprises, for input nucleotide symbol strings representing input data to be encoded as nucleotides, converting the input nucleotide symbol strings to constrained nucleotide symbol strings completely representing the input nucleotide symbol strings and satisfying a coding constraint; after converting the input nucleotide symbol strings to the constrained nucleotide symbol strings, calculating a redundancy code for the constrained nucleotide symbol strings, wherein the redundancy code carries redundancy information for the constrained nucleotide symbol strings and comprises a plurality of redundancy code nucleotide symbols; and incorporating the redundancy code nucleotide symbols of the redundancy code and the constrained nucleotide symbol strings into result nucleotide symbol strings, wherein the result strings satisfy a relaxed version of the coding constraint, completely represent the input nucleotide symbol strings, and comprise the redundancy information for the constrained nucleotide symbol strings.

In another embodiment, a method comprises, for input nucleotide symbol strings representing sequencing data to be decoded as output digital data, recovering a plurality of redundancy code nucleotide symbols carrying redundancy information and systematically interleaved throughout the input nucleotide symbol strings; for the input nucleotide symbol strings representing sequencing input data to be decoded as output digital data, recovering a plurality of underlying nucleotide symbol strings; applying the redundancy information of the redundancy code nucleotide symbols to the underlying nucleotide symbol strings, wherein the applying results in correction or verification of the underlying nucleotide symbol strings.

In another embodiment, one or more computer-readable media comprise computer-executable instructions capable of causing a computing system to receive a plurality of input nucleotide symbol strings representing underlying data; computer-executable instructions capable of causing the computing system to, for a given input nucleotide symbol string out of the input nucleotide symbol strings, compare an observed length to an expected length; computer-executable instructions capable of causing the computing system to, responsive to determining that the given input nucleotide symbol string is exactly one symbol too long or short, correcting an insertion or deletion error within a main symbol string portion of the given input nucleotide symbol string via a redundancy coding extracted from the given input nucleotide symbol string; computer-executable instructions capable of causing the computing system to verify integrity of the corrected main symbol string portion of the given string via a second redundancy code interleaved within the main symbol string portion of the given string; and computer-executable instructions capable of causing the computing system to recover outer coding redundancy information interleaved across main portions of nucleotide symbol strings comprising the corrected, verified main portion of the given string; applying the outer coding redundancy information across the main portions of the nucleotide symbol strings, resulting in further corrected nucleotide symbol strings; and decoding a constrained encoding of the further corrected nucleotide symbol strings.

The foregoing and other objects, features, and advantages will become more apparent from the following detailed description, which proceeds with reference to the accompanying figures.

DETAILED DESCRIPTION

Example 1—Overview

Figure 1:
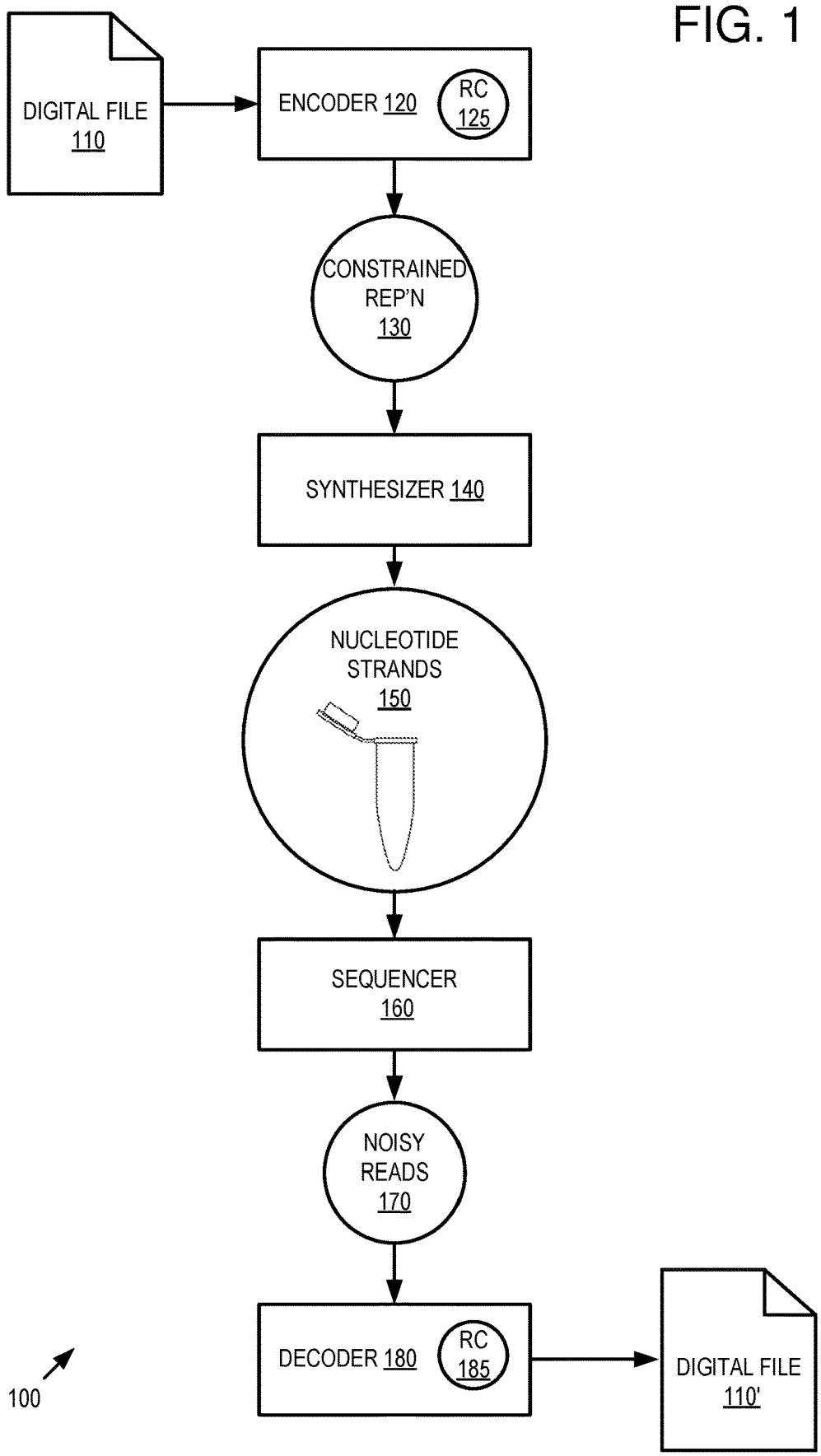
FIG. 1 is a block diagram of an example system implementing reverse concatenation of error-correcting codes in DNA data storage.

A number of reverse concatenation technologies for encoding data in a DNA storage context are described herein. Such technologies can be useful generally in DNA storage scenarios because of their error-resistant nature.

Notably, the error profile of DNA data storage can be quite different from that of conventional digital data. Therefore, new approaches to redundancy are needed to address error processing.

Encoding data in DNA strands typically involves introducing three types of redundancy: constrained representation (on individual strands), inner redundancy (on individual strands), and outer redundancy (across strands).

Combining any kind of coding with constrained representation can be challenging. For example, if traditional constrained encoding techniques are employed (e.g., "normal concatenation"), redundancy information is generated before the constrained encoding is applied. However, such an approach necessarily results in applying the constrained encoding to the redundancy information itself.

Subsequently, during decoding, due to the nature of the constrained encoding, an error in the input can propagate to more than one unit of the redundancy information, thereby limiting its usefulness. The phenomenon is not limited to redundancy information. An error in any strand can be amplified when the constrained representation is unwound, creating more errors to be corrected by an outer code. Due to the prevalence of errors in a DNA storage context, such a phenomenon can be harmful, demanding more redundancy, which equates to more materials and time and, ultimately, higher cost.

A naive solution is to attempt to perform the constrained encoding first and then calculate the redundancy information, which is then appended to the underlying data. However, there is no guarantee that the redundancy information will meet the constraint of the constrained encoding; therefore, the purpose of constraining the data is defeated (i.e., it does not meet the constraint).

As described herein, a number of different technologies can be applied in reverse concatenation scenarios that result in mere relaxation of the original constraint. If the relaxed version of the constraint is acceptable, the technologies described provide a useful encoding of data that both incorporates redundancy features that are useful as well as is resistant to error, especially error propagation due to the decoding process.

As described herein, a basic form of reverse concatenation can be used to address substitution errors. A further enhancement can be used to also address insertion/deletion errors.

Because the technologies relate to encoding and decoding data, they can be applied across a large number of use cases involving DNA data storage and retrieval.

Example 2—Example Terminology

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes for using nucleotide bases to represent digital information. See e.g., Grass et al., "Robust Chemical Preservation of Digital Information on DNA in Silica with Error-Correcting Codes," 54 Angew. Chem. Int. Ed. 2552 (2015) and Organick et al., "Random access in large-scale DNA data storage," 36:3 Nat. Biotech. 243 (2018). Advantages of using DNA rather than another storage media for storing digital information include information density and longevity. DNA data storage can improve information density, longevity, and accessibility. The contents of the disclosure may be used with any type of polynucleotide such as DNA, RNA, and DNA-RNA hybrids, thus references to "DNA" are illustrative and not intended to limit the application to only DNA or to only use of natural nucleotide bases.

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the reverse complement of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention DNA for the sake of brevity and readability, but RNA may be used in place of or in combination with DNA. RNA may also bind to DNA forming a hybrid molecule.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

"Hybridizing" as used herein means placing two complementary single-strand (ss) (or partially single-strand) DNA strands in conditions that allow hybridization to form a double-strand (ds) DNA strand or causing two complementary ssDNA strands to hybridize and form a dsDNA strand. Hybridization may be performed under high stringency conditions.

Artificial synthesis of DNA allows for creation of DNA strands with arbitrary series of the nucleotides. The order in which individual monomers of these four nucleotides are assembled together into a polymer can represent information in an analogous manner as 0 and 1 in digital computers. Thus, multiple DNA strands can be synthesized with particular orders of the four DNA nucleotides and encode large amounts of information. The information is encoded as a series of DNA nucleotides, but may represent any type of data such as text, audio files, video files, or anything else that may be encoded by conventional binary data recording in electronic computers.

The term "primer" as used herein refers to an oligonucleotide which is capable of acting as a point of initiation of nucleic acid synthesis when placed under conditions in which synthesis of a primer product, which is complementary to a nucleic acid strand, is induced, e.g., in the presence of four different nucleotide triphosphates with appropriate enzymes at a suitable temperature and salt concentration. Specific length and sequence will depend on the complexity of the required primer targets, as well as on the conditions of primer use such as temperature and ionic strength. In some implementations, a primer can be 5-50 nt, 10-25 nt, or 15-20 nt in length. The fact that amplification primers do not have to match exactly with the corresponding template sequence to warrant proper amplification is amply documented in the literature. It is generally accepted that a typical length of PCR primers is 18-22 nt. This length is long enough for adequate specificity and short enough for primers to bind easily to the template at the annealing temperature.

The term "amplifying" which typically refers to an exponential increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including polymerases and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art.

One technique for amplification is PCR which may use a PCR thermocycler. A variety of PCR techniques are known and can be used with the techniques described herein. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of Thermus species, including, but not limited to *Thermus aquaticus* (Taq), *Thermus flavus* (Tfl), and *Thermus thermophilus* (Tth), as well as the Kienow fragment of DNA polymerase I and the HIV-1 polymerase.

The entire contents of a DNA pool, or other vessel containing the DNA to be analyzed, may be placed in a PCR thermocycler. The process of PCR is well-known to those skilled in the art and has been extensively characterized. PCR involves the following three steps: denaturation, annealing, and extension. First, any dsDNA is denatured, converting to single strands. The primers are then annealed to the complementary regions of the single stranded molecules. In the third step, the primers are extended by the action of the DNA polymerase. All these steps are temperature sensitive and a common choice of temperatures is 94° C., 60° C., and 70° C., respectively. In order to amplify the sequencing adaptors together with the designated DNA, the primers are designed to hybridize with the ends of the sequencing adaptors in order to create multiple copies of the ligation products. Melting Temperature ($T_m$) by definition is the temperature at which one half of a DNA duplex will dissociate to become single stranded and indicates the duplex stability. Primers with melting temperatures in the range of 52-58° C. generally produce the best results. Primers with melting temperatures above 65° C. have a tendency for secondary annealing. The GC content of the sequence gives a fair indication of the primer $T_m$. Other DNA strands from the DNA pool will still be present during PCR, but primers present in the PCR mix will be unlikely to hybridize with those DNA strands. The selectively amplified DNA generated by the PCR thermocycler may be provided to a DNA sequencer. PCR amplification prior to sequencing improves the yield and may convert ssDNA to dsDNA which improves the stability and longevity of DNA in storage.

Example 3—Example System Implementing Reverse Concatenation of Error-Correcting Codes in DNA Data Storage FIG. 1 is a block diagram of an example system 100 implementing reverse concatenation of error-correcting codes in DNA data storage. In the example, the system 100 encodes a digital file 110 that is ultimately decoded as a copy 110' of the digital file 110.

The digital file 110 is typically a binary representation of underlying data of any arbitrary format. The encoder 120 accepts the digital file 110 as input and outputs a constrained representation 130 of the digital file that meets a relaxed version of a particular constraint as described herein. As described herein, the encoder 120 can implement reverse concatenation functionality 125 to advantage.

The resulting constrained representation 130 can take the form of ordered nucleotide symbol strings.

A nucleotide synthesizer 140 accepts the constrained representation 130 as input and generates nucleotide strands (e.g., oligonucleotides) 150 according to the nucleotide symbol strings of the constrained representation 130. At this point, the strands are logically ordered because they include an address; however, physically, the strands can be mixed together in an unordered fashion.

Subsequently, the physical material of the nucleotide strands 150 can be read by a sequencer 160 which ultimately outputs noisy reads 170 that are attempted reconstructions of the original input nucleotide symbol strings of the constrained representation 130.

A decoder 180 accepts the noisy reads 170 and generates a reconstructed copy 110' of the original digital file 110. As described herein, the decoder 180 can include functionality 185 for decoding strings that have been encoded using reverse concatenation technologies as described herein.

The encoder 120 can be implemented on a computing system, as can the decoder 180. In practice, encoding and decoding can be performed on the same computing system or on separate computing systems. For example, one party may encode the digital file 110 and then provide the nucleotide sequences 150 to another party, which performs decoding.

The goal of encoding/decoding process is to have an exact copy of the data emerge from the encoding/decoding process. However, in practice, it can be challenging to address errors introduced by synthesis and sequencing. Such errors can result in substitutions, deletions, and insertions. Accordingly, redundancy information is included in the encodings. As described herein, reverse concatenation technology can address the particular challenges introduced by also addressing coding constraints as described herein.

In practice, the systems shown herein, such as system 100, can vary in complexity, with additional functionality, more complex components, and the like. Additional components can be included to implement security, redundancy, load balancing, report design, and the like.

The described computing systems can be networked via wired or wireless network connections, including the Internet. Alternatively, systems can be connected through an intranet connection (e.g., in a corporate environment, government environment, or the like).

The system 100 and any of the other systems described herein can be implemented in conjunction with any of the hardware components described herein, such as the computing systems described below (e.g., processing units, memory, and the like). In any of the examples herein, the digital files, nucleotide symbol strings, redundancy symbols, insertion/deletion-sensitive sequences, noisy reads, and the like can be stored in one or more computer-readable storage media or computer-readable storage devices. The technologies described herein can be generic to the specifics of operating systems or hardware and can be applied in any variety of environments to take advantage of the described features.

Figure 2:
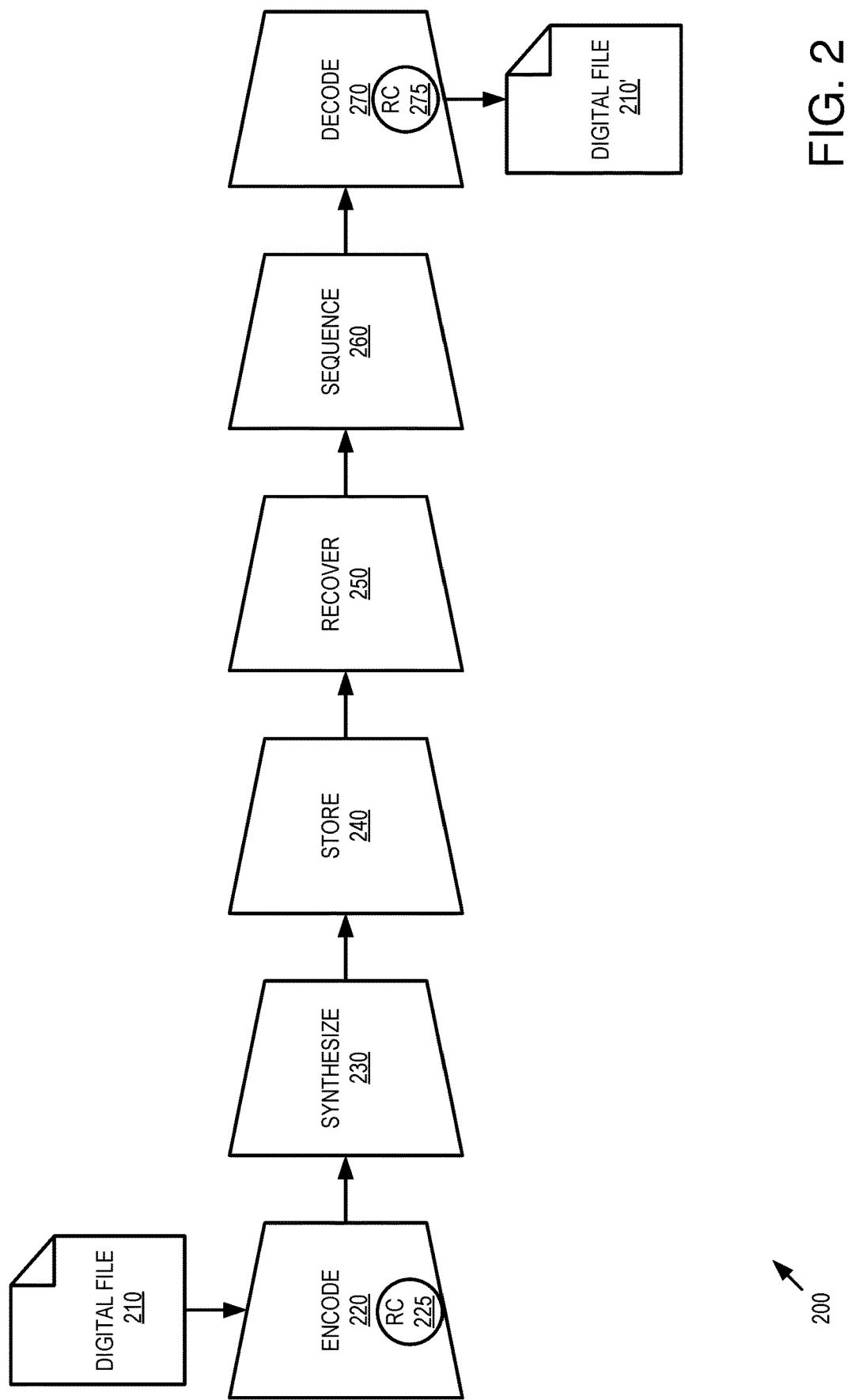
FIG. 2 is a flowchart of an example method of implementing reverse concatenation of error-correcting codes in DNA data storage.

Example 4—Example Method Implementing Reverse Concatenation of Error-Correcting Codes in DNA Data Storage FIG. 2 is a flowchart of an example method 200 of implementing reverse concatenation of error-correcting codes in DNA data storage and can be performed, for example, by the system of FIG. 1.

At 220, a digital file 210 is encoded using reverse concatenation 225 as described herein. The resulting output is nucleotide symbol strings, which are synthesized into nucleotide strands (e.g., oligonucleotides) at 230. In practice, multiple copies of each strand can be synthesized.

The physical nucleotide strands can be stored at 240 and subsequently recovered at 250. In practice, amplification can be used to increase the number of copies of the strands, whether before or after storage or both.

At 260, the input nucleotide sequences can be sequenced (i.e., read), resulting in output nucleotide symbol strings (e.g., noisy reads) that are decoded at 270 using decoding techniques 270 that recognize reverse concatenation, resulting in a copy 210' of the digital file 210.

In practice, a single party may perform all the acts shown; however, it is also possible that a single party only performs some actions (e.g., on the encoding side) while another party performs others (e.g., on the decoding side). Division of tasks may also take place along domain lines (e.g., one party performs the digital calculations while another performs the wetware functions of synthesis and sequencing).

The method 200 and any of the other methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

The illustrated actions can be described from alternative perspectives while still implementing the technologies.

Example 5—Example DNA Data Storage Scenarios

Binary data of the kind currently used by computers to store text files, audio files, video files, software, and the like can be represented as a series of nucleic acids in a polynucleotide (i.e., DNA or ribonucleic acid (RNA)). There are multiple techniques for representing the 0 and 1 of binary data as a series of nucleotides. A polynucleotide sequence is designed to hold the binary data and then synthesized with an oligonucleotide synthesizer. The synthesized polynucleotide is placed into storage, it is ultimately read by a polynucleotide sequencer. The data generated by the polynucleotide sequencer is decoded to recover the stored binary data. The machines that write and read the sequences of polynucleotides are not 100% accurate and introduce errors. Some types of errors, such as insertions, deletions, or substitutions of a nucleotide, can be identified and corrected. Other types of errors, in particular "bursty" errors in which there are multiple errors in a localized "burst" adjacent or close to each other, can be difficult or impossible to correct.

Example 6—Example Digital File

In any of the examples herein, a digital file can take the form of digital information of any arbitrary format or length. In practice, any information representable in digital form can be stored by the digital file (e.g., image, sound, video, text, hypertext, database, attribute, markup language, object notation, application files, executable content, compressed data, and the like).

The digital file can be converted to a nucleotide symbol string by encoding it as quaternary data (e.g., in a quaternary alphabet). Such encoding can take different forms, such as using A, C, G, and T to represent different combinations of 1's and 0's (e.g., A represents 00, C represents 01, G represents 10, and T represents 11 or the like); a one-hot encoding can be used (e.g., one nucleotide symbol represents 1, and the others represent 0); or the like. The nucleotide symbol string can be implied based on the digital data (e.g., actual A's, C's, G's, and T's need not be stored as long as there is a way to differentiate between them).

In any of the decoding examples herein, a resulting quaternary string can be decoded to recover the original digital data.

However, as described herein, such a raw encoding is typically not suitable for synthesis of nucleotide strands for a number of reasons. For example, redundancy is typically needed to address errors, and a constrained encoding may be desired to better accommodate synthesis and/or sequencing technologies.

To facilitate storage in spite of errors that inevitably occur during DNA synthesis, storage, and sequencing, data coding includes redundancy as described herein.

Example 7—Example Nucleotide Symbol Strings

In any of the examples herein, a nucleotide symbol string can take the form of a string of nucleotide symbols. In practice, a set of strings representing a digital file can be logically arranged in a grid-like format. For example, rows can represent a string, and the rows are stacked on top of each other, forming columns. However, the logical arrangement or notation can vary depending on circumstances.

After the strings are synthesized as physical nucleotide strands, they are placed into a storage medium and lose their ordering. To preserve logical ordering, an address can be included on the string/strand.

Subsequently, when strings are recreated from the strands during the sequencing process, they can be ordered according to the address. Thus, the strings can be ordered during the decoding process to recreate the original grid-like format.

Due to currently available technology, the nucleotide symbol strings described herein typically take a length of 100-500 nt. However, as technology evolves, the length can be expected to increase. As shown herein, the initial length is typically shorter than the ultimate length due to the addition of constrained encoding, redundancy, address information, primers for amplification, and the like.

Although examples describe nucleotide strings for DNA, implementations using RNA, synthetic nucleotides, or some combination thereof can also be implemented.

In practice, a nucleotide symbol string (e.g., a row in a grid of strings) ultimately represents a nucleotide strand (e.g., a molecule). So, the terms "string" and "strand" can identify the same sequence of nucleotides, where one is stored in digital memory, and the other is stored in DNA.

Example 8—Example Encodings

In any of the examples herein, a variety of encodings can be used to transform data from an unencoded state to an encoded state. The data can then subsequently be transformed via decoding back to its original state. Encodings can also be used to generate redundancy information that does not transform input data as described herein.

Transformational encodings include those that impose a constraint on nucleotide symbol strings, or so-called "constrained encodings." Depending on the specific technologies employed for DNA synthesis and sequencing, to avoid catastrophic errors, encoding can be done so that strands exhibit a specific structure. A common type of such structure is a bound on the length of homopolymer runs for example, a strand where homopolymer run length is bounded by 2, a DNA strand cannot have 3 or more repeated occurrences of the same nucleotide. Other forms of constrained representation may include having different bounds for the length of allowed homopolymer runs for different bases. Such a constraint can be imposed, for example, due to difficulty in accurately synthesizing or sequencing a strand for a string that violates the constraint.

So, in a case where a constrained encoding is to impose a constraint that no more than 1 nucleotide value can appear in a row (e.g., there are no consecutive nucleotide symbols that have the same value), the constrained encoder can transform any arbitrary input nucleotide symbol string into one that does not have more than one identical nucleotide value in a row. Typically, such a string is of longer length due to the encoding process and is sometimes called a "constrained nucleotide symbol string" to reflect that it has been encoded with a constrained encoding.

The constrained nucleotide symbol string completely represents the original string, and decoding can unwind the encoding to recover the original string in its entirety.

As described herein, it may be possible that a relaxed version of the constraint is ultimately acceptable. So, for example, perhaps a homopolymer run of two consecutive identical symbol values is acceptable instead of only one. As described herein, the reverse concatenation can result in a relaxed version of the particular constraint of a constrained encoding when the encoding process is performed on a string meeting the particular constraint.

A possible relationship between the original constraint and relaxed version of the constraint is that the original coding constraint limits homopolymer runs to n consecutive instances, and the relaxed version limits homopolymer runs to n+1 instance (where n is an integer greater than 0). However, other implementations are possible as described herein.

In practice, a constrained representation can be applied in different ways. For example, an encoding can map the entire raw data as a very long string to a constrained representation and then partition the resulting long string into strands. Or the encoding can first partition the data into small pieces corresponding to individual strands, and then apply the constrained coding to the individual pieces.

Example 9—Example Redundancy

In any of the examples herein, another type of encoding produces redundancy information. Such redundancy information can be used for error-correction or integrity verification of the data for which it is produced.

Two broad classes of redundancy information include inner redundancy (e.g., the redundancy information is for data within a nucleotide symbol string) and outer redundancy (e.g., the redundancy information is for data across a plurality of nucleotide symbol strings).

Inner redundancy information can be generated for a string and then later used to correct the string and/or verify its integrity. Such inner redundancy information can take the form of additional nucleotide symbols that do not carry new information but are derived from the nucleotide symbols of the underlying strand. Such redundancy facilitates integrity verification or error correction of the strand.

Outer redundancy information can be generated across strings and then later used to correct the data and/or verify its integrity. Outer redundancy can be particularly useful in the DNA data storage context because errors often tend to cluster and/or be localized within a string. Redundancy across strings is thus orthogonal to the usual error patterns produced by synthesis and/or sequencing and can therefore recover information that inner coding cannot. Like in a redundancy information, outer redundancy information can take the form of additional nucleotide symbols that do not carry new information but is derived from the nucleotide symbols of the underlying cross-strand symbols. Such redundancy facilitates error correction where certain strands experienced catastrophic errors or are entirely missing from the output of the sequencing process.

The specific technique used to implement redundancy can vary. For example, a Reed Solomon code, LT code, or an LDPC code can be used. Hamming codes can also be employed.

Redundancy can also be classified according to whether it corrects/detects substitution errors or insertion/deletion errors. In any of the examples herein where not otherwise noted, redundancy can correct or detect substitution errors, but some examples also correct or detect insertion/deletion errors as described. Insertions and deletions are particularly important in a DNA data storage context because synthesis and/or sequencing can introduce such errors, which are atypical in conventional digital processing.

Redundancy that can both correct errors as well as verify integrity can be desirable in nanopore sequencing scenarios due to the higher error rate exhibited by such technologies.

Example 10—Example System Encoding via Reverse Concatenation

Figure 3:
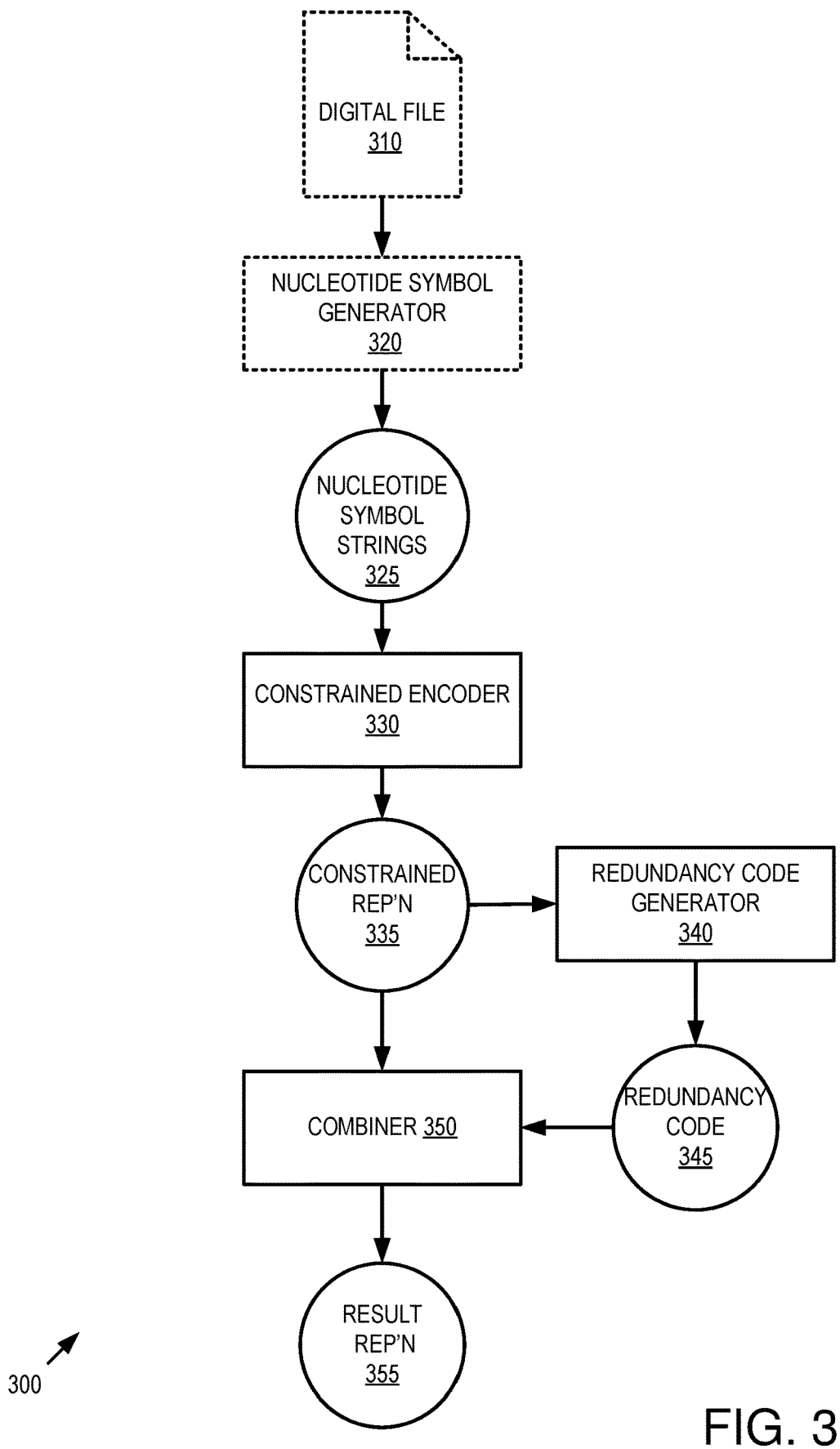
FIG. 3 is a block diagram of an example system encoding nucleotide symbol strings into a result representation with redundancy information via reverse concatenation.

FIG. 3 is a block diagram of an example system 300 encoding nucleotide symbol strings into a result representation with redundancy information via reverse concatenation that can be used in any of the examples herein. For purposes of context, it is noted that a nucleotide symbol generator can take a digital file 310 as input and generate nucleotide symbol strings 325. Such generation can use any number of encodings to transform digital data (e.g., 1's and 0's) into quaternary data (e.g., representing A's, C's, T's, and G's) according to a number of available encodings.

A constrained encoder 330 can accept the nucleotide symbol strings 325 as input and generate a constrained representation 335 of the nucleotide symbol strings 325. As described herein a constrained representation 335 can take the form of nucleotide symbol strings (e.g., typically longer than the strings 325) that meet one or more specified constraints. If desired, the constrained representation 335 can also include reserved nucleotide symbol spaces for redundancy information as described herein.

In a reverse concatenation scenario, a redundancy code generator 340 can accept the constrained representation 335 as input and generate redundancy code (e.g., nucleotide symbols) for error detection and/or correction.

A combiner 350 can accept both the constrained representation 335 and the redundancy code 345 as input and output a result representation 355, which has both the constrained representation and the redundancy code contained therein and takes the form of nucleotide symbol strings.

Although not shown, additional information (e.g., address information) can be added to the resulting nucleotide symbol strings to assist in reconstruction of the original digital file 310.

It should be noted that a constrained coding need not be applied to the redundancy code 345. As described herein, the redundancy code 345 can be included in a way that may disrupt the constraint of the constrained encoding imposed by the encoder 330, but the resulting representation 355 still complies with a relaxed version of the constraint.

The scenario is sometimes called "reverse concatenation" because the redundancy code is calculated after the constrained representation is applied to the input nucleotide symbols, which ordinarily results in possible violation of the constraint imposed by the constrained encoder. Traditional concatenation typically adds the redundancy symbols in before the constrained encoding is calculated, thereby applying the constrained encoding to the redundancy symbols, which can lead to additional error propagation during decoding. Unwinding a constrained representation typically results in propagation of an error from one encoded symbol to multiple unencoded symbols.

Example 11—Example Method of Encoding via Reverse Concatenation

Figure 4:
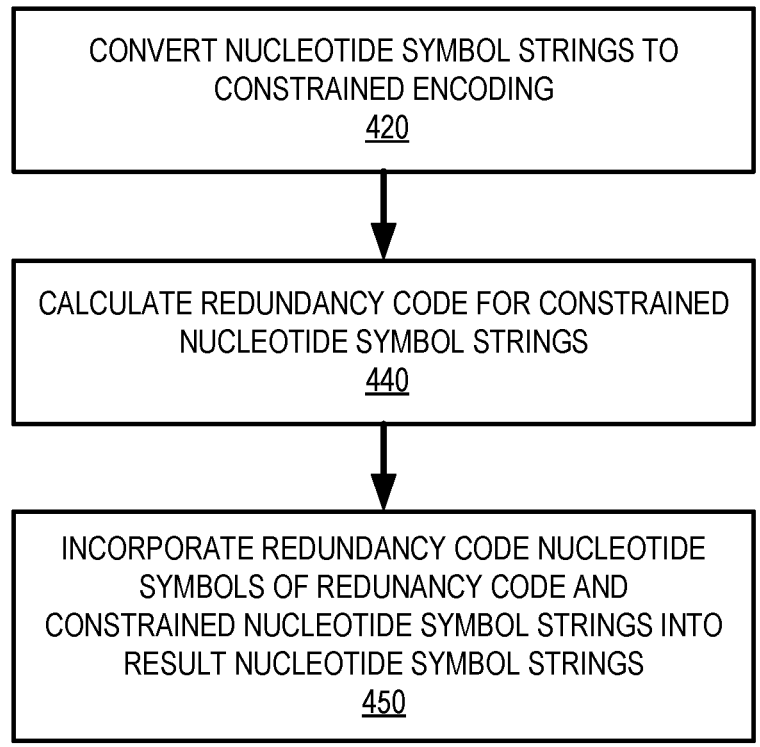
FIG. 4 is a flowchart of an example method of encoding nucleotide symbol strings into a result representation with redundancy information via reverse concatenation.

FIG. 4 is a flowchart of an example method 400 of encoding nucleotide symbol strings into a result representation with redundancy information via reverse concatenation that can be used in any of the examples herein for encoding and can be performed, for example, by the system of FIG. 3.

The method 400 can receive nucleotide symbol strings (e.g., nucleotide symbol strings 325) representing a digital file as described herein. In the encoding scenario, nucleotide symbol strings represent input data to be encoded as nucleotides.

At 420, the input nucleotide symbol strings are converted to a constrained encoding (e.g., a constrained encoding is applied to the nucleotide symbol strings), which takes the form of constrained nucleotide symbol strings. As described herein, such a constrained encoding can satisfy a particular constraint and completely represent the input set of nucleotide symbol strings (and the digital file).

At 440, a redundancy code is calculated for the constrained nucleotide symbol strings. As described herein, such a redundancy code can correct substitution errors and can be an outer code, an inner code or both. The redundancy code can take the form of nucleotide symbols (e.g., redundancy code nucleotide symbols) that contain redundancy information about the constrained nucleotide symbol strings. As described herein, the redundancy code calculation and subsequent incorporation can be performed after constraining the input strings, thus the term "reverse" concatenation.

At 450, the redundancy code nucleotide symbols of the redundancy code and the nucleotide symbols of the constrained nucleotide symbol strings are incorporated into result nucleotide symbol strings. Such result nucleotide symbol strings thus include both the symbols from the redundancy code and the symbols from the constrained nucleotide symbol strings. As described herein, due to the reverse concatenation nature of the method, the constrained encoding has not been applied to the redundancy code symbols. Still, the result strings satisfy a relaxed version of the coding constraint. The strings completely represent the input nucleotide symbol strings and comprise the redundancy information of the constrained nucleotide symbol strings.

In practice, additional information such as address information or additional redundancy information can be added to the result nucleotide symbol strings before synthesis.

Example 12—Example Relaxed Version of Constraint

In any of the examples herein, application of the reverse concatenation technologies can produce result strings that no longer satisfy the particular constraint that was imposed by the constrained encoding. For example, because the constrained encoding has not been applied to the redundancy code symbols, including them in the result nucleotide symbol strings can result in violation of the particular constraint.

However, as noted herein, the result nucleotide symbol strings can still satisfy a relaxed version of the particular constraint. Thus reverse concatenation can still be used in scenarios where a relaxed version of particular constraint is acceptable. In practice, a system can be designed from the outset with the relaxed version of the particular constraint in mind, and the particular constraint imposed by the constraint encoding can intentionally be made more stringent then required. Therefore, at the end of the process, the resulting nucleotide symbol strings meet the desired level of constraint.

As a result, the advantages of reverse concatenation can be enjoyed while still conforming with a desired level of constraint.

Example 13—Example Method of Decoding Strings Formed via Reverse Concatenation

Figure 5:
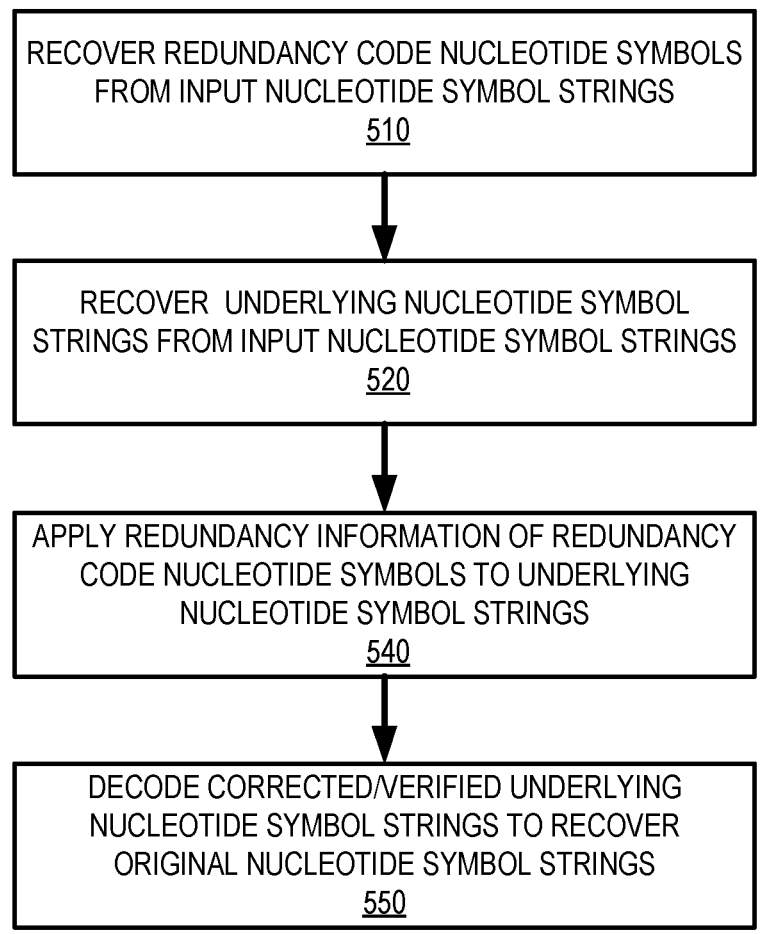
FIG. 5 is a flowchart of an example method of decoding nucleotide symbol strings that have been encoded via reverse concatenation.

FIG. 5 is a flowchart of an example method 500 of decoding nucleotide symbol strings that have been encoded via reverse concatenation that can be used in any of the examples herein and can be performed, for example, to decode information encoded by the system of FIG. 3. As described herein, the process can be performed to decode information encoded using reverse concatenation technologies, which is typically recovered by sequencing nucleotide strands synthesized based on a method such as that shown in FIG. 4. In practice, amplification can be used so that there is more than one copy of any given strand; therefore, the decoding process can account for multiple copies. For ordering, an address can be placed on the strand, which is then recovered during sequencing and used to order the resulting strings.

The method accepts input nucleotide symbol strings representing sequencing data (e.g., output by a sequencer) to be decoded as output digital data.

The input set of nucleotide symbol strings can comprise respective addresses indicating an order of the strings. The strings can thus be ordered according to the addresses before recovering the redundancy symbols and underlying strings (e.g., so that the interleaving can be correctly aligned as appropriate).

At 510, the method recovers redundancy code nucleotide symbols from the input nucleotide symbol strings. For example, the method can determine which of the nucleotide symbols in the input nucleotide symbol strings are redundancy symbols. As described herein such redundancy symbols can be systematically interleaved in locations throughout the input nucleotide symbol strings so that they can be recovered during decoding. Such redundancy symbols can represent an outer or inner code (or both) as described herein and carry redundancy information (e.g., for the underlying nucleotide symbol strings, that can be of constrained encoding).

At 520, the underlying nucleotide symbol strings (e.g., which can be of constrained form) are recovered from the input nucleotide symbol strings. For example, the method can determine which of the nucleotide symbols in the input nucleotide symbol strings are underlying nucleotide symbols of nucleotide symbol strings. As described herein, such underlying nucleotide symbol strings can be encoded with a constrained encoding and completely represent the original data file. However, due to possible errors introduced during the synthesis and sequencing processes, such nucleotide symbol strings often include errors.

At 540, the redundancy information of the redundancy code nucleotide symbols is applied to the underlying nucleotide symbol strings. For example, such redundancy information can be used to verify integrity of the underlying nucleotide symbol strings and/or correct them. Thus, applying results in correction or verification of the underlying nucleotide symbol strings. As described herein, the constrained code has not been applied to the redundancy information. As a result, a constrained decoding process need not be applied to the redundancy information. Such an arrangement has technical advantages because the constrained decoder can result in propagation of errors across more than one output symbol. Therefore, although there may be an error in the redundancy code, its effect can be limited by employing reverse concatenation as described herein.

Again, the result of applying the redundancy information can be a set of corrected or verified constrained nucleotide symbol strings. At 550, the corrected/verified underlying nucleotide symbol strings are decoded to recover the original nucleotide symbol strings. In other words, the constrained encoding is unwound.

At this point, the quaternary code of the original nucleotide symbol strings can be converted back to the ones and zeros representing the digital file.

Example 14—Example Interleaving

In any of the examples herein, an interleaving can be used to achieve reverse concatenation during encoding, which then affects the decoding process as well.

Incorporating redundancy code nucleotide symbols into result nucleotide symbol strings can comprise interleaving reserved symbol spaces into constrained nucleotide symbol strings and placing the redundancy code nucleotide symbols into the reserved symbol spaces.

In practice, a systematic recurrence of spaces can be used because it can then be easily recreated on the decoding side. Distribution of the reserved nucleotide spaces within the target strings (e.g., across columns, across rows, etc.) can be uniform to avoid localized errors. Although shown in a recurring 2-s-3-s pattern in some examples herein, other patterns can be used instead (e.g., every i or the like).

Thus, recurring positions for the reserved nucleotide symbol spaces can be systematically calculated.

The frequency of the spaces depends on the rate of the redundancy code that is to be used. For example, if the redundancy code has 25% redundancy, then every 5th symbol can be a space. If the redundancy code has 50% redundancy, then every 3rd symbol can be a space. In some cases multiple redundancies can be incorporated, leading to different results.

Although examples herein show a size of one, the size (e.g., how many symbols long) of the reserved nucleotide symbol spaces can also be varied as described herein. The reserved nucleotide symbol spaces can thus accommodate holding more than one symbol. Or, another way of describing such a scenario is that reserved nucleotide symbol spaces of size one can be placed apart from each other (e.g., size of one) or grouped together (e.g., size of greater than one). Grouping the spaces together (spaces having a size greater than one) can result in further relaxation of the constraint, but can be helpful when increased redundancy is desired.

Thus, in any of the examples herein, at least one of the reserved nucleotide symbol spaces can have a size of greater than one symbol.

Alternatively, the interleaving can simply be described as interleaving the redundancy code nucleotide symbols into constrained nucleotide symbol strings.

In practice, additional interleaving can be performed (e.g., the strands themselves are interleaved to address bursty error conditions).

Figure 6:
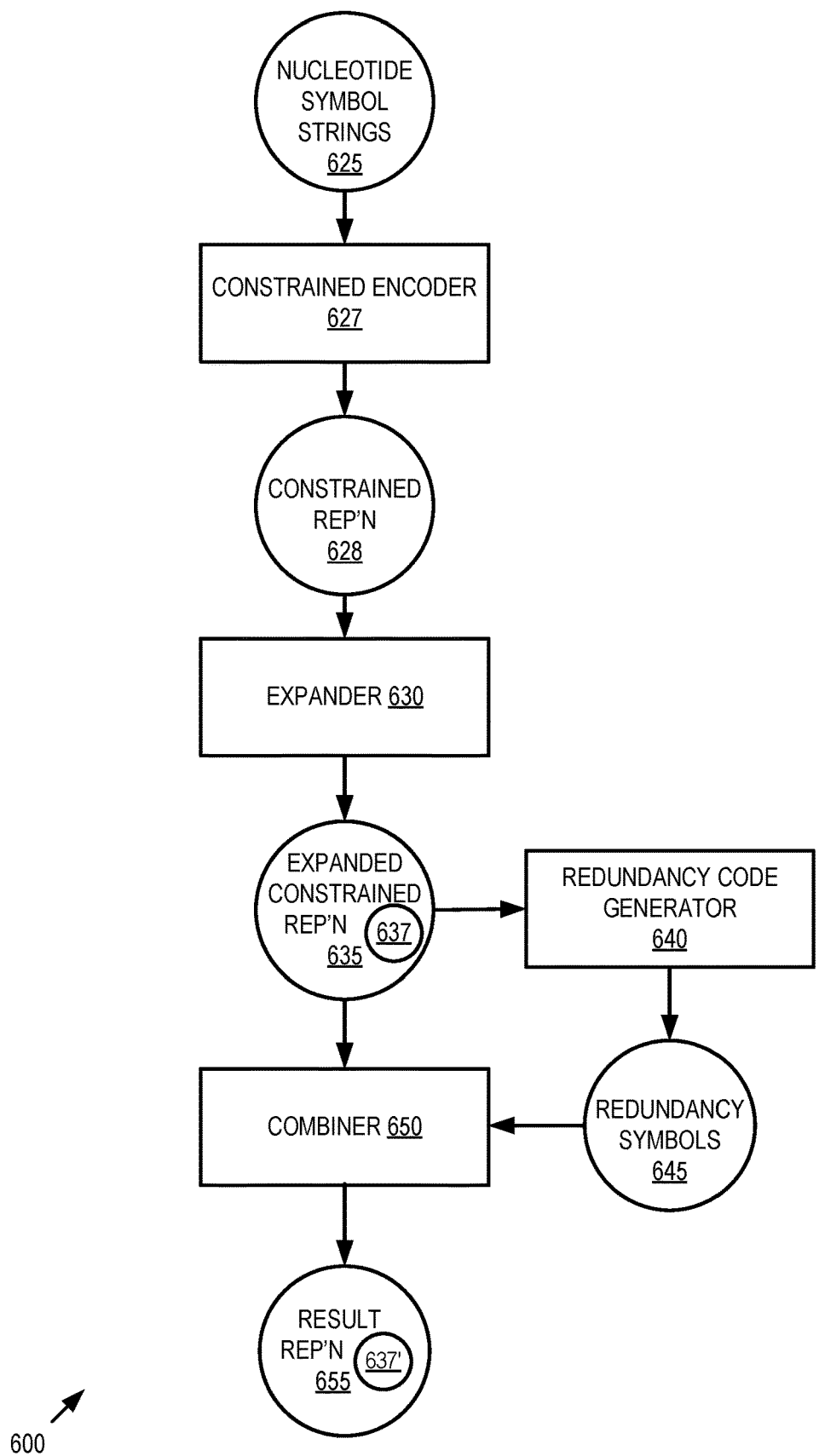
FIG. 6 is a block diagram of an example system encoding nucleotide symbol strings into result nucleotide symbol strings via interleaved reserved nucleotide symbol spaces.

Example 15—Example System Encoding via Interleaved Reserved Nucleotide Symbol Spaces FIG. 6 is a block diagram of an example system 600 encoding nucleotide symbol strings into result nucleotide symbol strings via interleaved reserved nucleotide symbol spaces. Such a system is a variation on the reverse concatenation technologies described herein and can be used for encoding in any of the examples described herein. The nucleotide symbol strings 625 can be output of a nucleotide symbol generator that takes a digital file as input.

The constrained encoder 627 can accept the nucleotide symbol strings 625 as input, apply a constrained code to them and output a constrained representation 628, which takes the form of nucleotide symbol strings.

The expander 630 can accept the constrained representation 628 and output an expanded constrained representation 635 that includes reserved nucleotide symbol spaces 637. In practice, the functionality of the constrained encoder 627 and the expander 630 can be combined into a single unit such that both the constrained representation 628 and the reserved nucleotide symbol spaces 637 are done at the same time (e.g., in parallel, serially, by streaming, or the like).

A redundancy code generator 640 can accept the expanded constrained representation 635 as input and output redundancy nucleotide symbols 645.

The combiner 650 can accept the redundancy nucleotide symbols 645 as input and insert them into the reserved nucleotide symbol spaces 637 of the expanded constrained representation 635, resulting in a result representation 655. The result representation 655 can take the form of nucleotide symbol strings and completely represents the digital file along with the redundancy information of the redundancy nucleotide symbols.

Thus the system 600 interleaves the reserved nucleotide symbol spaces 637 into the constrained representation and places the redundancy nucleotide symbols 645 into the reserve nucleotide symbol spaces 637. In other words, the redundancy code nucleotide symbols 645 are interleaved into the constrained representation 628. As described herein, the interleaving can be performed in such a way that the result representation 655 still satisfies a relaxed version of the constraint that was used when encoding the constrained representation, even though the constrained encoding was not applied to the redundancy symbols 637' that reside in the result 655.

Figure 7:
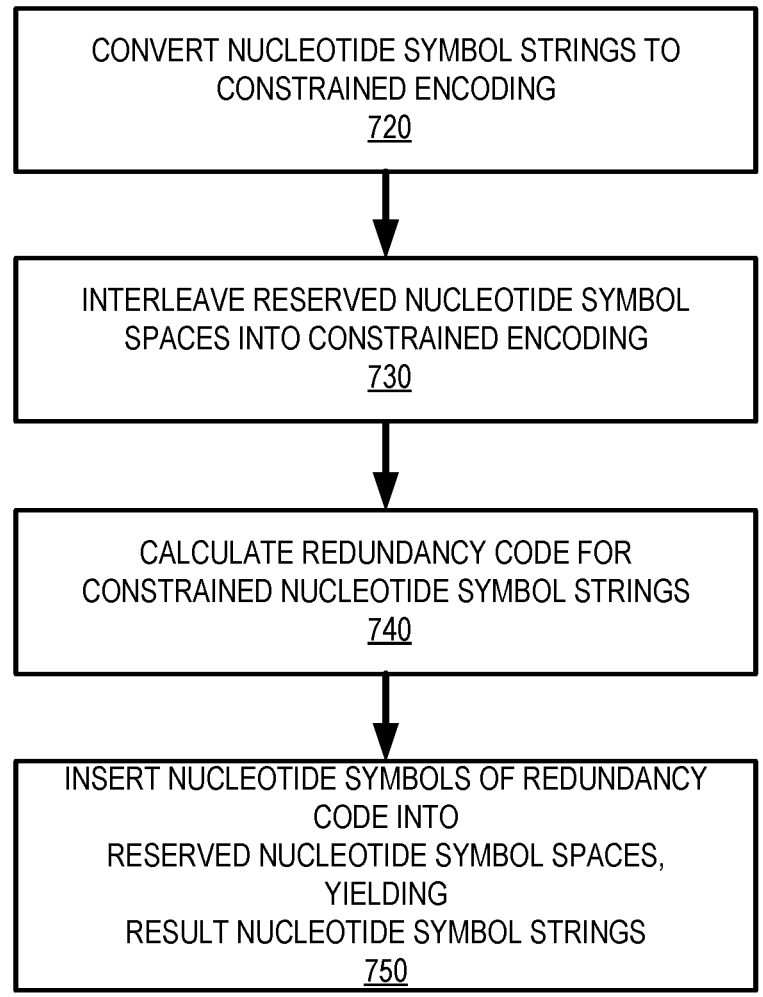
FIG. 7 is a flowchart of an example method of encoding nucleotide symbol strings into result nucleotide symbol strings via interleaved reserved nucleotide symbol spaces.

Example 16—Example Method of Encoding via Interleaved Reserved Nucleotide Symbol Spaces FIG. 7 is a flowchart of an example method 700 of encoding input nucleotide symbol strings into result nucleotide symbol strings via interleaved reserved nucleotide symbol spaces that can be used in any of the examples herein for encoding and can be performed, for example, by the system of FIG. 6.

At 720, the input nucleotide symbol strings are converted to a constrained encoding.

At 730, reserved nucleotide symbol spaces are interleaved into the constrained encoding.

At 740, a redundancy code is calculated for the constrained nucleotide symbol strings. The redundancy code takes the form of nucleotide symbol strings.

At 750, The nucleotide symbols of the redundancy code are inserted into the reserved nucleotide symbol spaces, yielding result nucleotide symbol strings. As a result, the nucleotide symbols of the redundancy code are interleaved into the constrained encoding.

Figure 8:
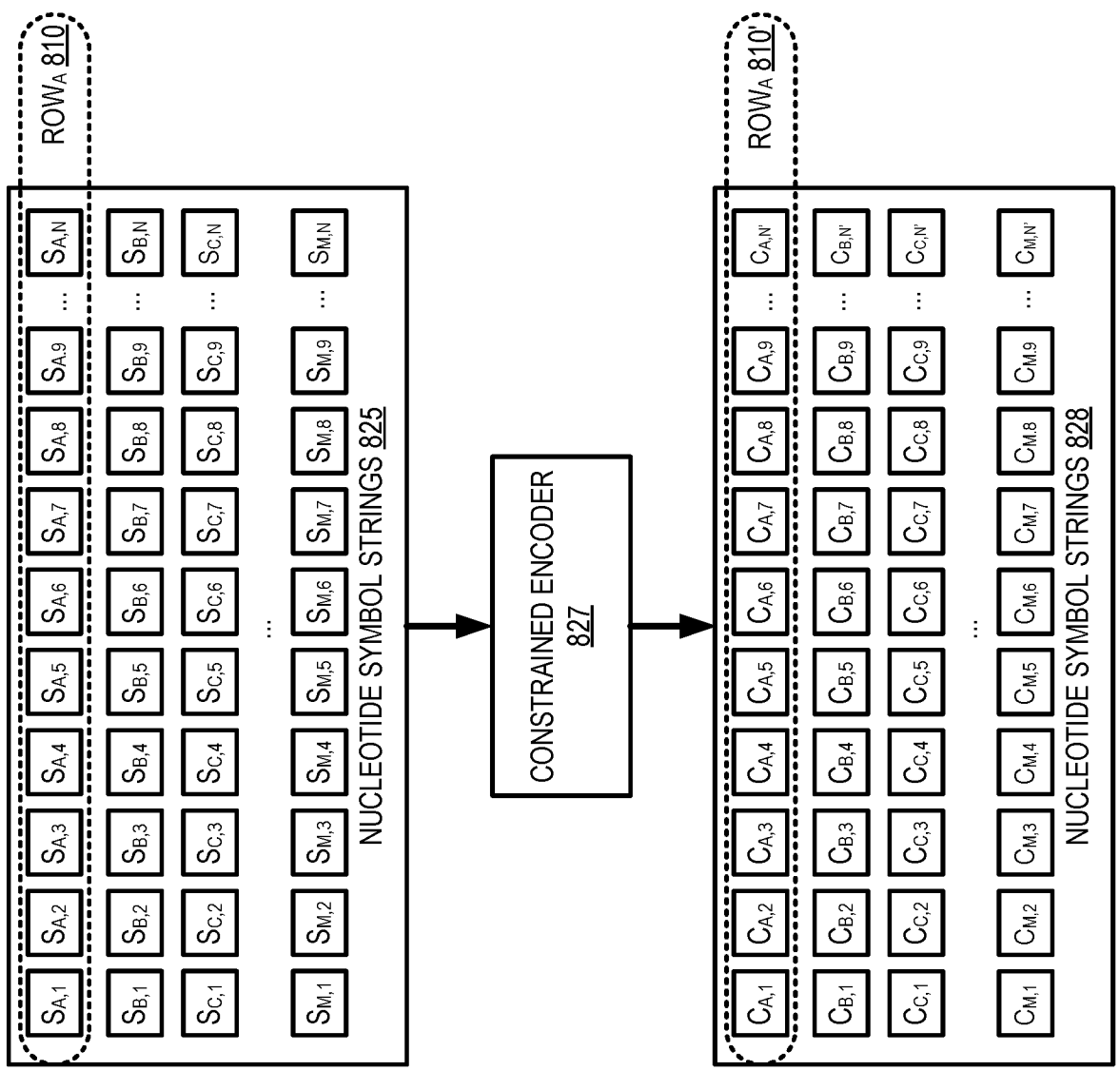
FIG. 8 is the first part a block diagram of an example encoder implementing interleaved reserved nucleotide symbol spaces.

Example 17—Example Encoder Implementing Interleaved Reserved Nucleotide Symbol Spaces FIG. 8 is the first part of a block diagram of an example encoder implementing interleaved reserved nucleotide symbol spaces that can be used for encoding in any of the examples herein. In the example, a constrained encoder 827 accepts nucleotide symbol strings 825 as input and outputs constrained nucleotide symbol strings 828.

The input nucleotide symbol strings 825 comprise a plurality of symbols arranged in logically ordered rows (e.g., $Row_A$ 810). Although the lengths of the strings are shown as being of length N, in practice they need not all be of exactly the same length. As described herein, a row represents a nucleotide strand. However, at this point, the row has not yet been fully prepared to be synthesized. As described herein, a constrained encoding can be applied to the row, redundancy information can be incorporated into the row, and other information may also be included (e.g., an address or the like).

The constrained nucleotide symbol strings 828 are typically somewhat longer then the input nucleotide symbol strings 825 as a result of the constrained encoding process. Again, although the lengths of the strings are shown as being N', in practice they need not all be of exactly the same length.

In the example, the number of rows remains the same. Therefore the number of strands will correspond to the number of rows in the input nucleotide symbol strings 825.

Figure 9:
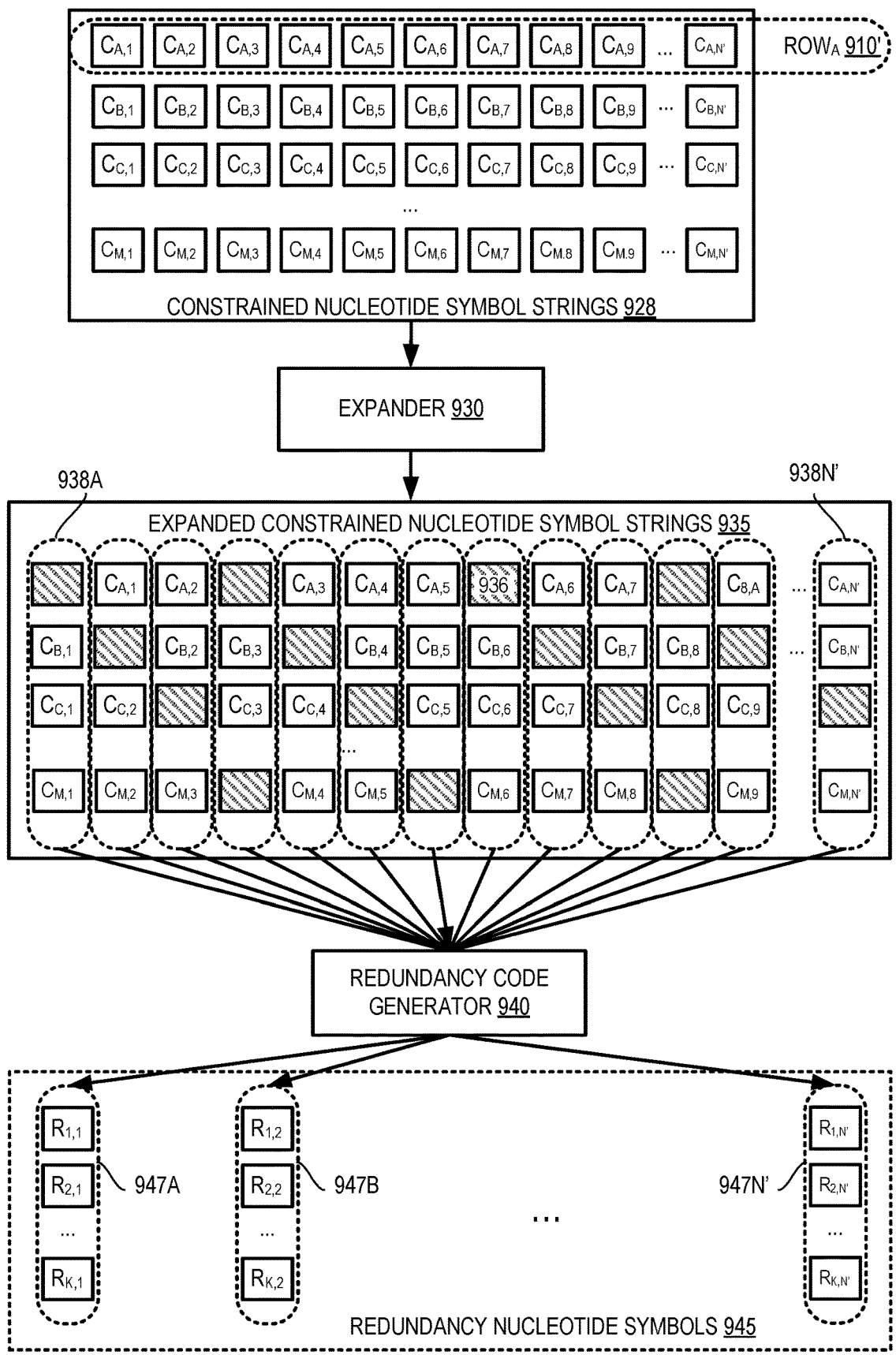
FIG. 9 is the second part of a block diagram of an example encoder implementing interleaved reserved nucleotide symbol spaces.

FIG. 9 is the second part of a block diagram of an example encoder implementing interleaved reserved nucleotide symbol spaces that can be used for encoding in any of the examples herein. The nucleotide symbol strings 928 (e.g., the strings 828 from the previous drawing) include a row 910' (e.g., the row 810' from the previous drawing) that is input to the expander 930 which produces the expanded constrained nucleotide symbol strings 935. As shown, the expander has interleaved reserved nucleotide symbol spaces (e.g., 936) into the constrained nucleotide symbol strings 928.

The redundancy code generator 940 accepts the expanded constrained nucleotide symbol strings as input and generates redundancy nucleotide symbols 945 as output. In the example, an outer encoding is applied; therefore, the generator 940 accepts columns 938A-N' of the nucleotide symbols as input and generates sets 947A-N' of redundancy symbols 945 for respective of the columns (e.g., each column has its own redundancy symbols). Thus the redundancy symbols 947A apply to (and are generated from) the column 938A. Such redundancy information is sometimes called "outer redundancy" because it calculates redundancy information across a plurality of strings and can be used to correct error or verify integrity of a span of symbols across the strings during decoding. However, in practice the redundancy information can be alternatively or additionally calculated within a string to generate inner redundancy information.

Figure 10:
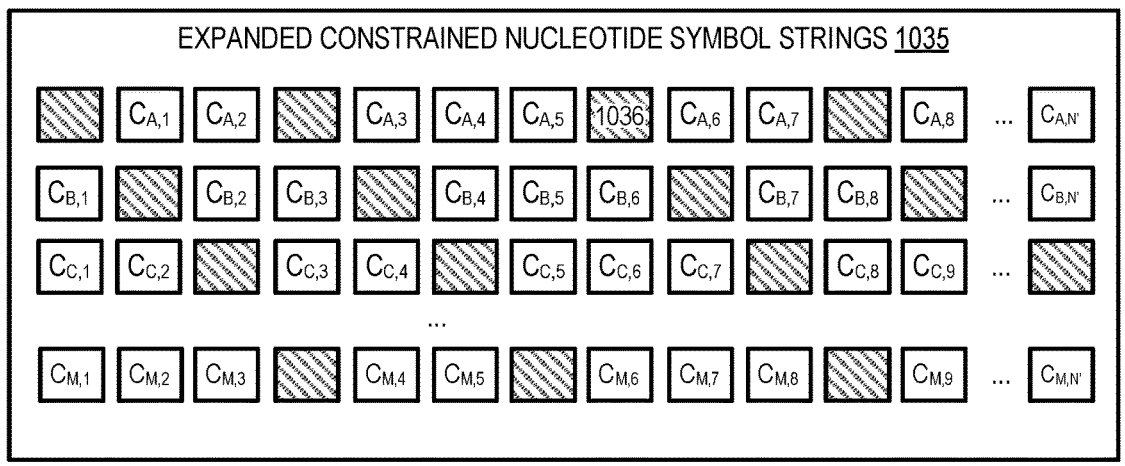
FIG. 10 is the third part of a block diagram of an example encoder implementing interleaved reserved nucleotide symbol spaces.
Figure 10:
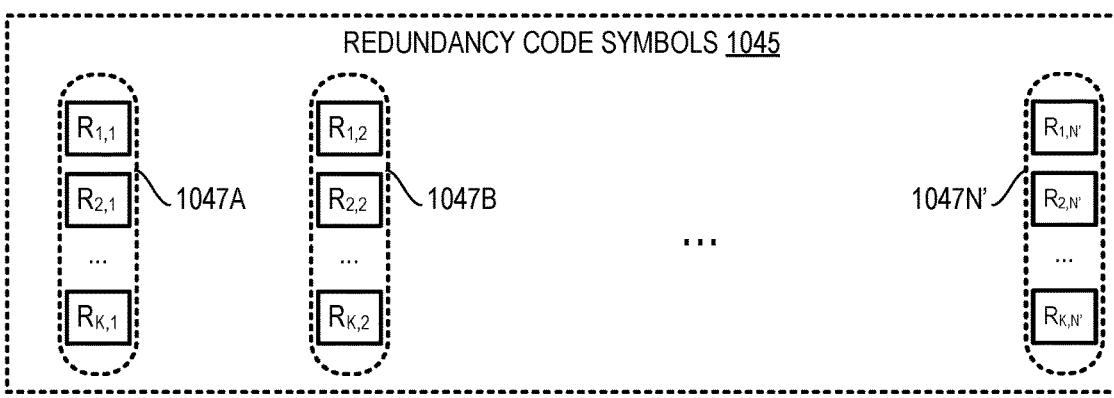
Figure 10:
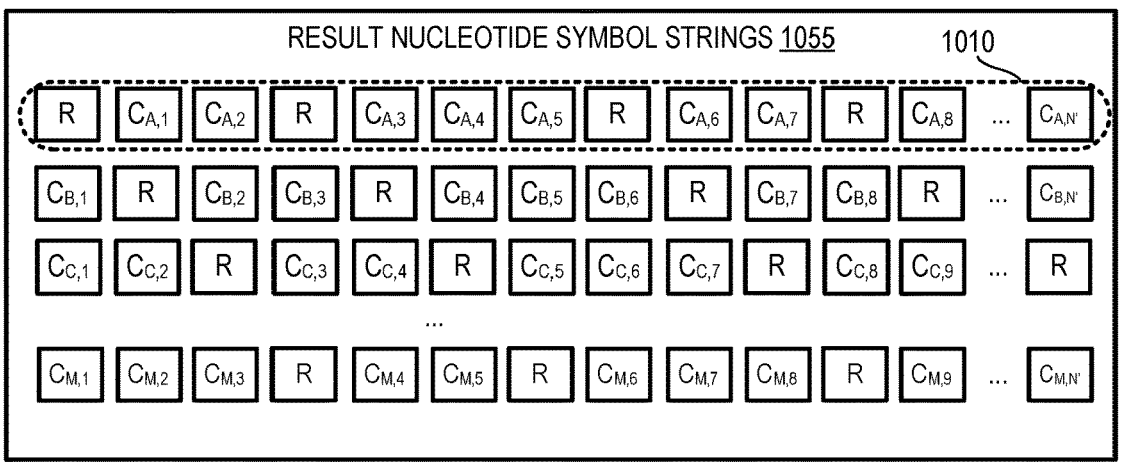

FIG. 10 is the third part of a block diagram of an example encoder implementing interleaved reserved nucleotide symbol spaces that can be used for encoding in any of the examples herein. The expanded constrained nucleotide symbol strings 1035 (e.g., 935) and redundancy code symbols 1045 (e.g., 945) comprising redundancy code symbols 1047A, 1047B, and 1047N' can be generated as shown in the previous two drawings.

The result nucleotide symbol strings 1055 can be generated by placing the redundancy code symbols 1045 into the reserved nucleotide symbol spaces (e.g., 1036). For inner redundancy codes, the symbols can be placed within the string for which the redundancy information is generated.

At this point, the constraint imposed by the constrained encoder may be violated; however, a relaxed form of the constraint is still satisfied. In other words, the nucleotide symbol string of row 1010 still satisfies a relaxed version of the constraint.

Figure 11:
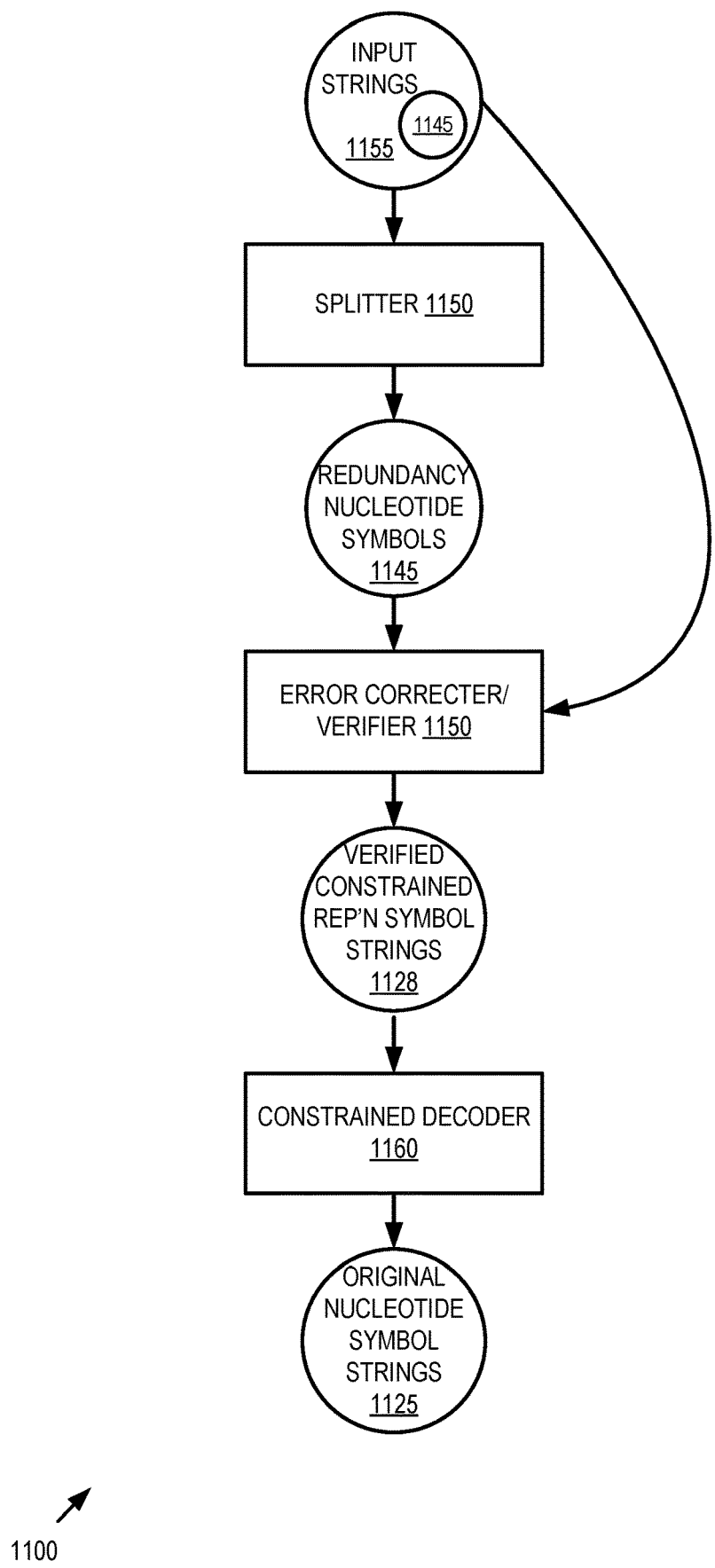
FIG. 11 is a block diagram of an example system decoding input strings implementing interleaved redundancy code nucleotide symbols.

Example 18—Example System Decoding Input Strings Implementing Interleaved Redundancy Code Nucleotide Symbols FIG. 11 is a block diagram of an example system 1100 decoding input strings implementing interleaved redundancy code nucleotide symbols that can be used for decoding in any of the examples herein. In the example, the decoder system 1100 accepts input strings 1155 derived from sequencing nucleotide strands that have been synthesized to represent the output of an encoding technique as described herein (e.g., the result representation 655 of FIG. 6). As described herein redundancy nucleotide symbols 1145 have been systematically interleaved within the input strings 1155. The decoder system 1100 ultimately outputs the original nucleotide symbol strings 1125 that were encoded as part of the encoding process, while using the redundancy nucleotide symbols 1145 for error correction and/or integrity verification.

In the example, a splitter 1150 accepts the input strings 1155 and outputs the redundancy nucleotide symbols 1145. As described herein the redundancy nucleotide symbols 1145 are not encoded by or input to a constrained coding. An error corrector/verifier 1150 receives both the redundancy nucleotide symbols 1145 and the input strings 1155 as input, and it outputs verified constrained representation nucleotide symbol strings 1128.

A constrained decoder 1160 accepts the verified constrained representation nucleotide symbol strings 1128 as input and outputs the original nucleotide symbol strings 1125, from which the original digital data can be recovered (e.g., by decoding the quaternary encoding). In other words, the constrained decoder 1160 unwinds the constrained encoding applied during the encoding process.

Figure 12:
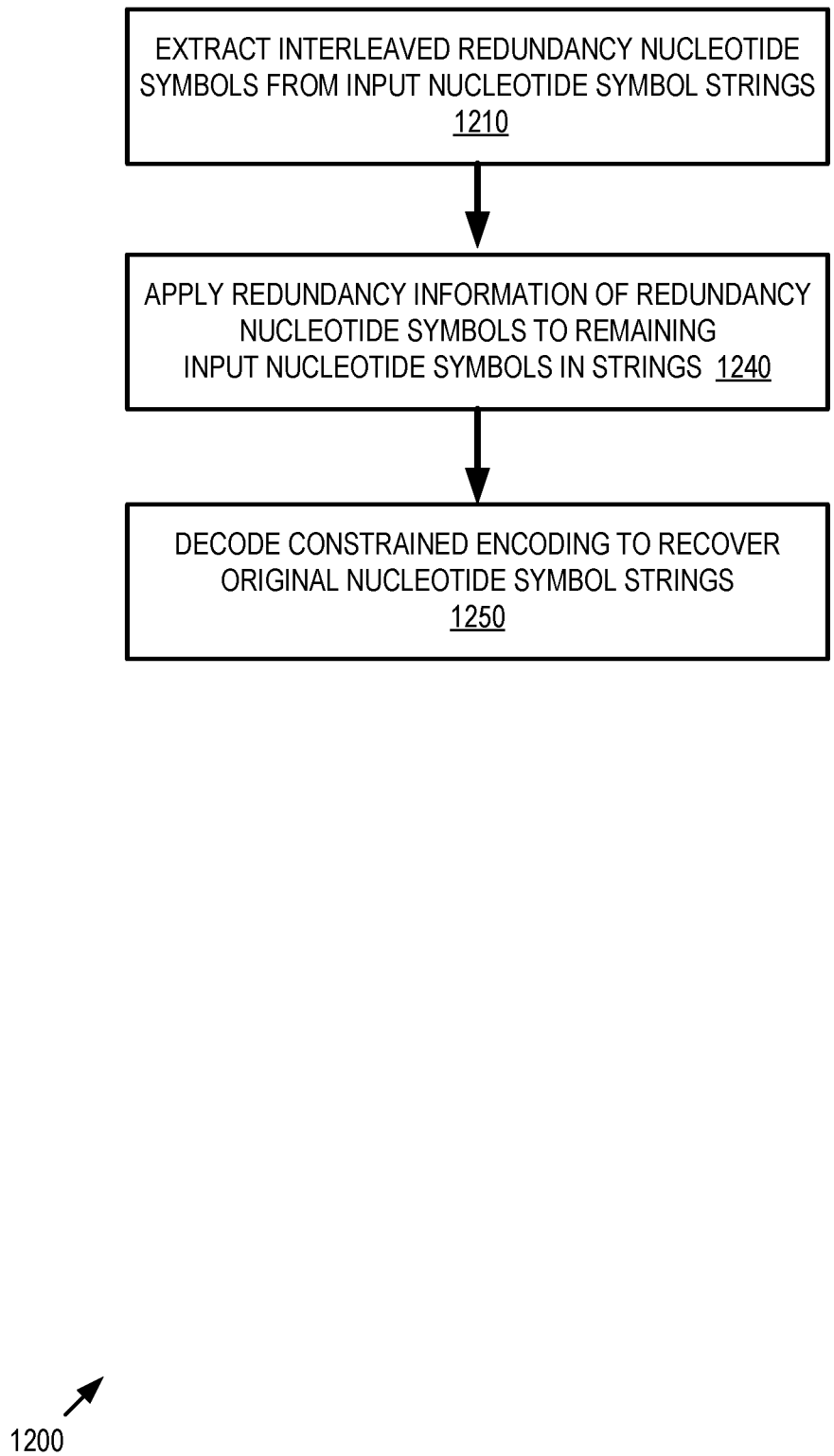
FIG. 12 is a flowchart of an example method of decoding input strings implementing interleaved redundancy code nucleotide symbols.

Example 19—Example Method of Decoding Input Strings Implementing Interleaved Redundancy Code Nucleotide Symbols FIG. 12 is a flowchart of an example method 1200 of decoding input strings implementing interleaved redundancy code nucleotide symbols that can be used in any of the examples herein for decoding and can be performed, for example, by the system of FIG. 11. In the example, The method 1200 accepts input strings as described herein (e.g., the input strings 1155 of FIG. 11).

At 1210, The interleaved redundancy nucleotide symbols are extracted from the input nucleotide symbol strings.

At 1240, the redundancy information of the redundancy nucleotide symbols are applied to the remaining nucleotide symbols of the input nucleotide symbol strings. As described herein such redundancy information can be used for error correction and/or integrity verification of the strings, which represents strands that have been sequenced. So at this point the nucleotide symbol strings are of a constrained format and have been error corrected and/or verified.

At 1250, the constrained encoding is decoded to recover the original nucleotide symbol strings. The original nucleotide symbol strings can then be used to recover the original data file.

Example 20—Example Table Demonstrating Relationships

Figure 13:
FIG. 13 is a table showing relationships between parameters.

FIG. 13 is a table 1300 showing relationships between parameters that can be used in any of the examples herein. The first column "maximum homopolymer run length" specifies a particular constraint to be met by encoded nucleotide symbol strings (e.g., there cannot be consecutive n polymers that have the same value). The "spacing" indicates the interleave spacing (e.g., how distant the reserved nucleotide symbol space are from each other). "Group size" indicates the size (e.g., number of symbols) occupied by a reserved nucleotide symbol space.

The "maximum final homopolymer run length" shows the relaxed version of the original constraint, and the "code redundancy" indicates the amount of redundancy that is incorporated into the encoded strings.

Thus, interleaving a single redundancy symbol every 4 spaces in an encoding that originally conformed to not-more-than-one-consecutive-homopolymer run length constraint results in a relaxed constraint of no-more-than-two-consecutive homopolymer run length constraint and 25% code redundancy.

The table 1300 demonstrates the flexibility of the reverse concatenation technologies in that they can accommodate a wide variety of constraints and code redundancy levels.

There is a limitation in that one cannot employ reverse concatenation if the longest allowed homopolymer run has to be of length 1.

One also cannot directly apply reverse concatenation in some circumstances in the setting of low rate (i.e., redundancy above 100%) outer codes because empty coordinates of strands cannot be spaced far enough from each other, and the increase in the length of the maximal homopolymer run would exceed one. However, such a limitation can be circumvented by placing reserved spaces on the strands in groups of size larger than one. Thus, reverse concatenation can be used even in low rate code scenarios at the expense of a more significant relaxation of the original representation constraint.

Example 21—Example Technologies Addressing Insertion/Deletion Errors

Reverse concatenation as described herein can be quite useful in addressing substitution errors; however, insertion/deletion errors can also be prevalent in DNA data storage scenarios. Accordingly, insertion/deletion redundancy can be incorporated into the reverse concatenation encoding process. However, there are challenges because adding additional bases produced by an inner encoding that addresses insertion/deletion errors would violate the representation constraints.

Figure 14:
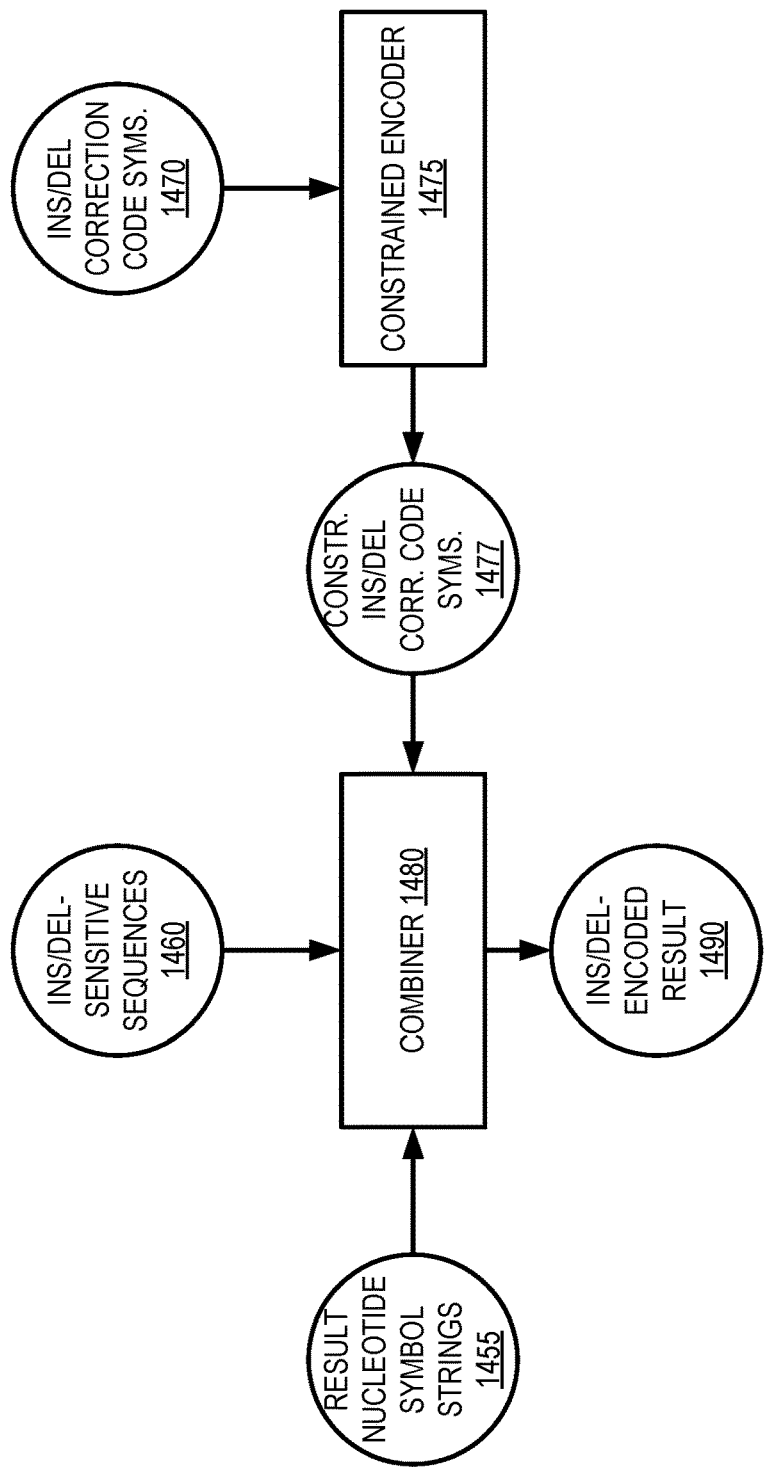
FIG. 14 is a block diagram of an example system encoding nucleotide symbol strings into result strings incorporating insertion/deletion redundancy information.

Example 22—Example System Encoding Incorporating Insertion/Deletion Redundancy FIG. 14 is a block diagram of an example system 1400 encoding nucleotide symbol strings into result strings incorporating insertion/deletion redundancy information that can be used in any of the examples herein.

In the example, the result nucleotide symbol strings 1455 can be constructed according to the reverse concatenation technologies described herein. In addition to accommodating an outer encoding, enough spaces can be reserved to also accept an inner encoding. Thus, both an inner and outer encoding can be interleaved in the result 1455 of reverse concatenation, which is used as an input to the system 1400.

A plurality of insertion/deletion-sensitive sequences 1460 can be calculated for the respective incoming strings 1455. Also, insertion/deletion correction code symbols 1470 can be calculated for the respective incoming strings 1455.

A constrained encoder can encode the insertion/deletion correction code symbols 1470 according to a constraint (e.g., the original constraint or a relaxed version of it), resulting in constrained insertion/deletion correction code symbols.

A combiner 1480 can accept the input strings 1455, the sequences 1460, and the symbols 1477 and append (e.g., concatenate) them into resulting strings (e.g., the input strings 1455, the sequences 1460, and the symbols 1477 for each string are appended together), resulting in the same number of output strings 1490, which meet the desired (e.g., relaxed) constraint.

Figure 15:
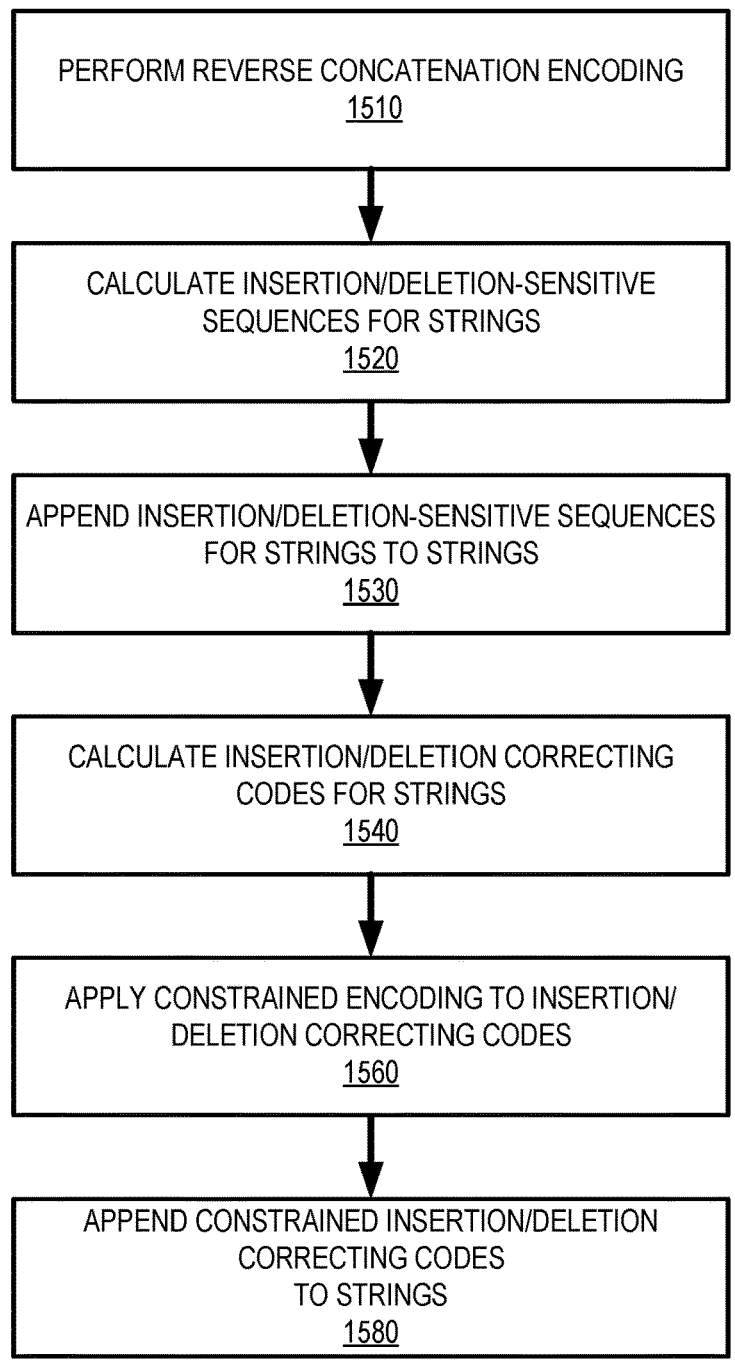
FIG. 15 is a flowchart of an example method of encoding nucleotide symbol strings into result strings incorporating insertion/deletion redundancy information.

Example 23—Example Method of Encoding That Incorporates Insertion/Deletion Redundancy FIG. 15 is a flowchart of an example method 1500 of encoding nucleotide symbol strings into result strings incorporating insertion/deletion redundancy information that can be used in any of the examples herein for encoding and can be performed, for example, by the system of FIG. 14.

In any of the examples herein, insertion/deletion correction codes for result nucleotide symbol strings can be calculated, the codes can be encoded with a constrained mapping. Insertion/deletion-sensitive sequences can be calculated for the result nucleotide symbol strings, and the constrained insertion/deletion correction codes and the insertion/deletion-sensitive sequences can be incorporated into the result nucleotide symbol strings.

At 1510, a reverse concatenation encoding is performed on underlying data, resulting in expanded constrained nucleotide symbol strings into which has been interleaved redundancy data.

At 1520, insertion/deletion-sensitive sequences are calculated for the nucleotide symbol strings. As described herein, such sequences can be dependent on the last nucleotide symbol in the string to which the sequence is appended.

At 1530, the insertion/deletion-sensitive sequences are appended to respective nucleotide symbol strings.

At 1540, insertion/deletion correcting codes are calculated for the expanded constrained nucleotide symbol strings.

At 1560, a constrained encoding is applied to the insertion/deletion correcting codes, resulting in constrained insertion/deletion correcting codes.

At 1580, the constrained insertion/deletion correcting codes are appended to the expanded constrained nucleotide symbol strings (e.g., after the insertion/deletion-sensitive sequences so that the constrained insertion/deletion correcting codes follow an insertion/deletion-sensitive sequence for a given string).

The resulting strings can then have additional information such as address added (e.g., prepended or appended), and the strings can be synthesized as nucleotide strands.

Figure 16:
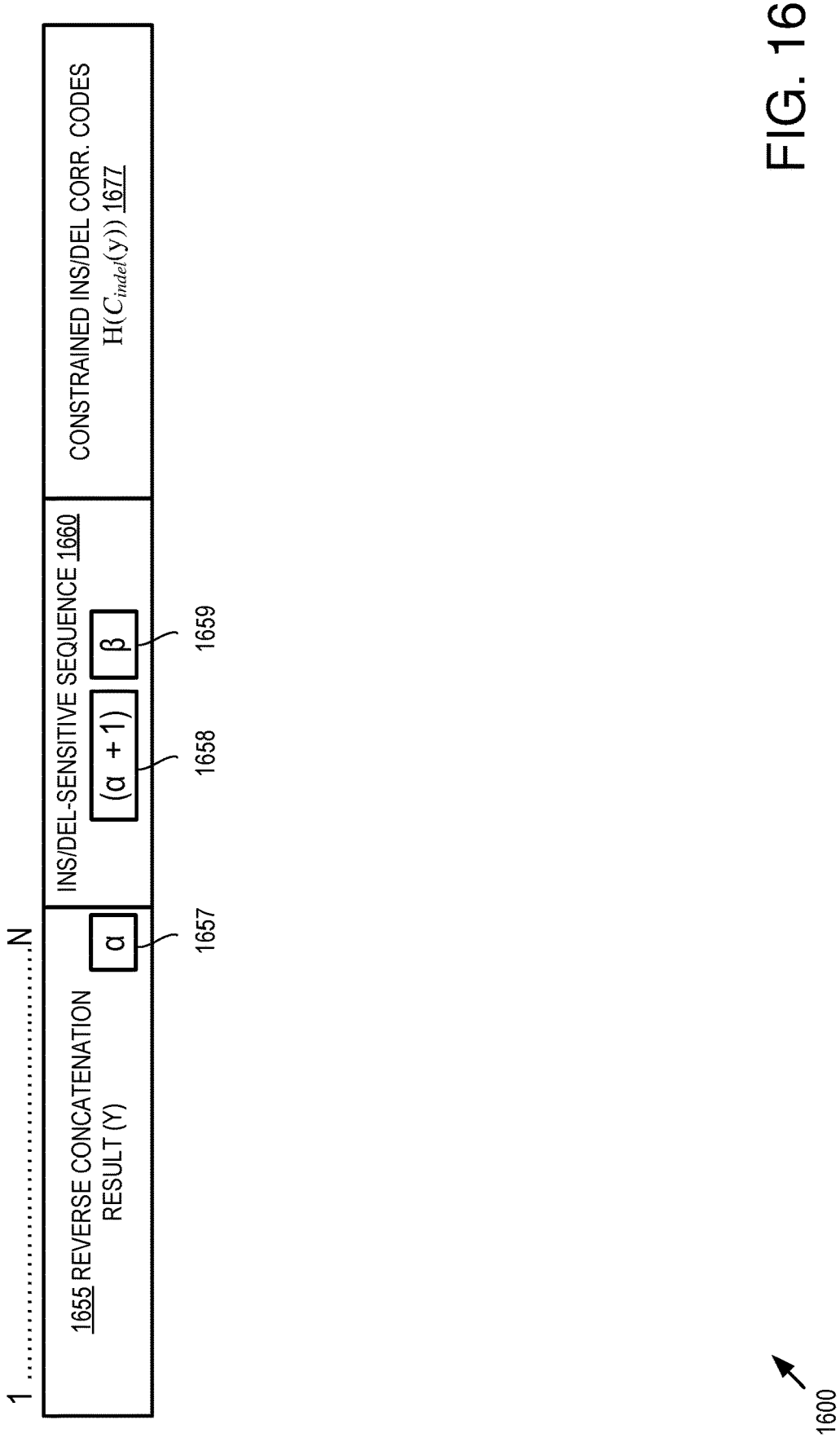
FIG. 16 is a block diagram of an example nucleotide symbol string incorporating insertion/deletion redundancy information.

Example 24—Example Nucleotide Symbol String Incorporating Insertion/Deletion Redundancy Information FIG. 16 is a block diagram of an example encoded nucleotide symbol string 1600 incorporating insertion/deletion redundancy information that can be used in any of the examples herein. In the example, a string 1600 comprises a reverse concatenation result (y) 1655 with a last symbol α 1657, an insertion/deletion-sensitive sequence 1660 with two calculated symbols (α+1) 1658 and β 1659, and constrained insertion/deletion correcting code nucleotide symbols 1677 calculated as described herein.

Although not shown, the strings can also include an address (e.g., a series of nucleotide symbols that indicate an orderable number) to assist in ordering.

The nucleotide symbol string 1600 can comprise three ingredients:

A systematic code $C_{subst}$ that can be used to correct a single substitution error of an associated string x during decoding. A Hamming or other similar code can be used. $C_{subst}(x)$ is vector of redundancy nucleotide symbols generated by an encoder of $C_{subst}$ on an input string x.

A mapping $C_{indel}$ that can, from a string x, produce a vector $C_{indel}(x)$ such that any single insertion or deletion in x can be corrected given access to the correct value of $C_{indel}(x)$. An example is described in Tenengolts, "Nonbinary codes, correcting single deletion or insertion," IEEE Transactions on Information Theory, vol. 30, no. 5, September 1984.

A mapping H can take a quaternary string and convert it into a desirable bounded homopolymer run length representation (e.g., that meets a desired constraint, such as a relaxed version of a constraint used to encode other data as described herein). The mapping H is thus a form of constrained encoding, but is also sometimes called a "constrained mapping."

When choosing locations of reserved nucleotide symbol spaces in strings, enough spaces can be placed to not only accommodate reverse concatenation of an outer code, but also interleave $C_{subst}(x)$ in the strings (e.g., a given string also includes $C_{subst}(x)$ for the string).

A nucleotide modulo function can be employed to assist in creation of the sequence 1660. Such a modulo function can define sequentialness for the sequence 1660. Nucleotide symbols (e.g., bases) A, C, G, and T can be mapped to integers 0, 1, 2, 3 mod (4) so that arithmetic operations can be performed on them. Adding one to A results in C, adding one to C results in G, adding one to G results in T, and adding one to T results in A. The selection of bases is arbitrary, and any mapping can be used as long as it is replicated during decoding.

The symbol $(\alpha+1)$ 1658 immediately follows $\alpha$ 1657 and has a value of $(\alpha+1)$ (e.g., if $\alpha$ is A, then $\alpha+1$ is C using the above mapping).

The symbol $\beta$ 1659 is an arbitrary nucleotide symbol that is different from $\alpha+1$, $(\alpha+2)$, and the first base of the constrained insertion/deletion correcting code nucleotide symbols 1677.

The resulting strand 1600 can thus take the form as follows:

$$y' = y \circ (\alpha+1) \circ \beta \circ H(C_{indel}(y)).$$

As described herein, the insertion/deletion-sensitive sequence 1660 can be used to advantage in light of possible insertion/deletion errors (e.g., during synthesis, sequencing, or the like).

Example 25—Example Decode Phenomena

In any of the examples herein, during decoding, more than one instance of a string for a particular address may be encountered. For example sequencing may output multiple copies of a strand. Due to errors introduced during synthesis and/or sequencing, the copies may not be exactly the same. As described herein, some strands (strings) can be discarded based on length, failure of integrity verification, and the like.

Further, the process of reconstructing the original strings from input strings from the sequencing process (the so called "trace reconstruction" of U.S. Patent Publication No. 2018/0 211 001 to Gopalan et al.) can be handled by a separate system. For example, the input nucleotide symbol strings can be clustered, and integrity/error/length information can be used to discard strings and/or determine how to cluster them. As the strings settle into clusters, it is then possible to reconstruct the likely original string for use in further decoding as described herein.

In some case, the redundancy information incorporated by the technologies described herein can be used to influence trace reconstruction.

Figure 17:
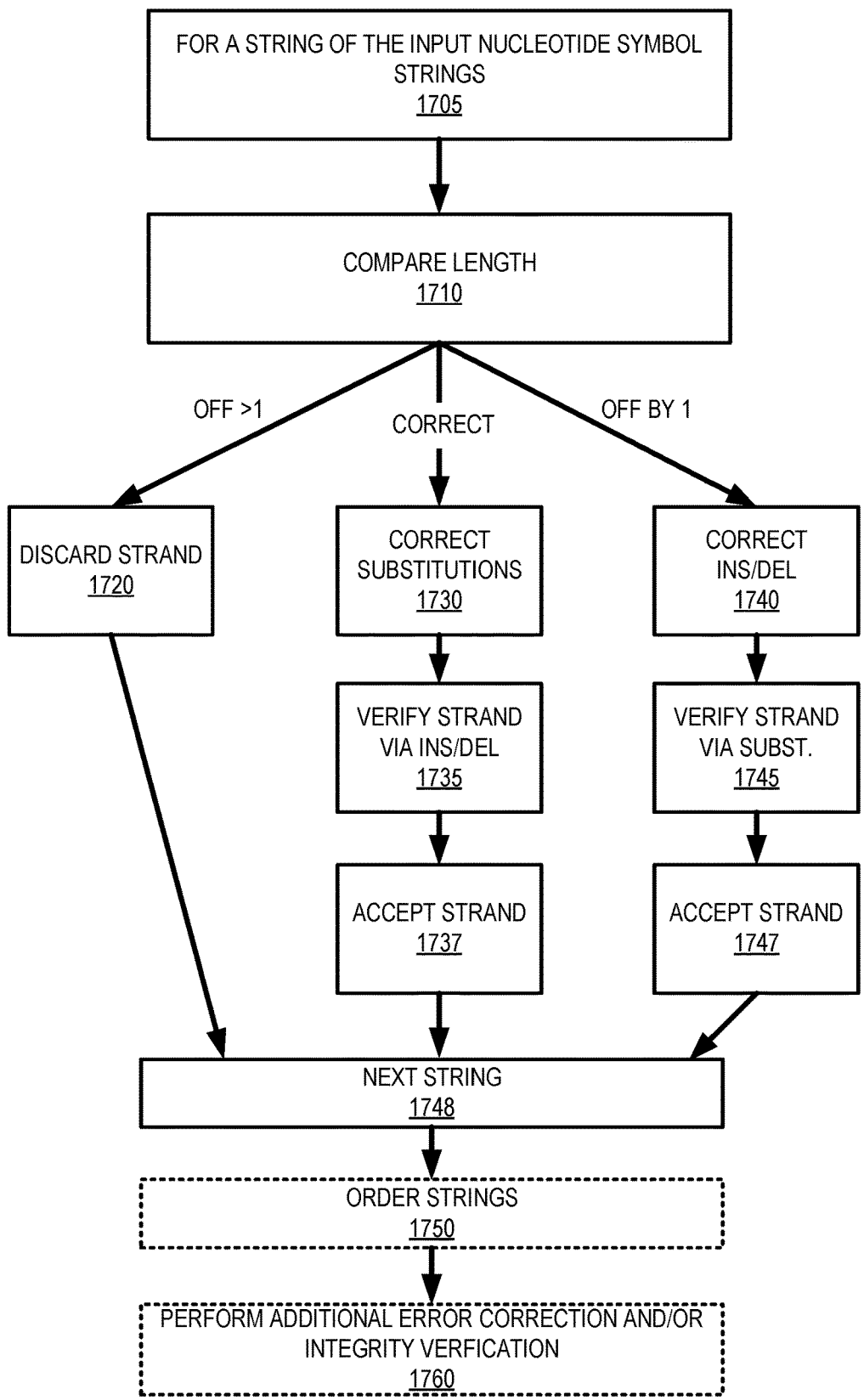
FIG. 17 is a flowchart of an example method of decoding a nucleotide symbol string incorporating insertion/deletion redundancy information.

Example 26—Example Decoding Method for Nucleotide Symbol String Incorporating Insertion/Deletion Redundancy FIG. 17 is a flowchart of an example method 1700 of decoding a nucleotide symbol string incorporating insertion/deletion redundancy information and can be performed to decode information encoded, for example, in the format shown in FIG. 16.

At 1705, the method starts with a given string out of the input nucleotide symbol strings. As described herein, redundancy symbols (e.g., outer and inner code) can be extracted from the string (y). $H(C_{indel}(y))$ can also be extracted and decoded to reveal $C_{indel}(y)$.

At 1710, the length of the input nucleotide symbol string is compared to its original length. For example, lengths can be fixed to a known size. A value indicating such a fixed length can be stored as file-level metadata.

If the length is found to be off by more than one symbol, the given string is discarded at 1720.

If the length is correct, at 1730, the interleaved substitution code can be extracted from the string and used to correct substitutions. The insertion/deletion correction symbols $C_{indel}(y)$ can be used to verify integrity of the strand at 1735. The strand is then accepted at 1737 if it passes integrity verification.

If the length is off by exactly 1, at 1740, $C_{indel}(y)$ can be used to correct an insertion or deletion error; integrity of the strand can be verified at 1745 via inner redundancy code $C_{subst}(y)$; and the strand can be accepted at 1747 if it passes integrity verification.

Further details of correcting deletions/insertions is provided below.

In practice, the method can continue 1748 to be performed for plural incoming strands that result from sequencing nucleotide strands into which data has been encoded according to the encoding technologies described herein. To facilitate decoding, the incoming strands are ordered 1750 according to an address on the strand.

Due to multiple synthesis and/or amplification, there can be numerous different instances of a strand that represents a row in the encoding. The method 1700 can be used to discard or accept strands. To further resolve ambiguities and differences among the plural instances, a clustering algorithm can be used to determine the underlying true data that was present in the original encoded strand.

Subsequently, further error correction or integrity verification can be performed 1760 on the ordered strands. For example, inner redundancy nucleotide symbols or outer redundancy nucleotide symbols can be employed during decoding as described herein.

Example 27—Example Deletion Case Detection

Figure 18:
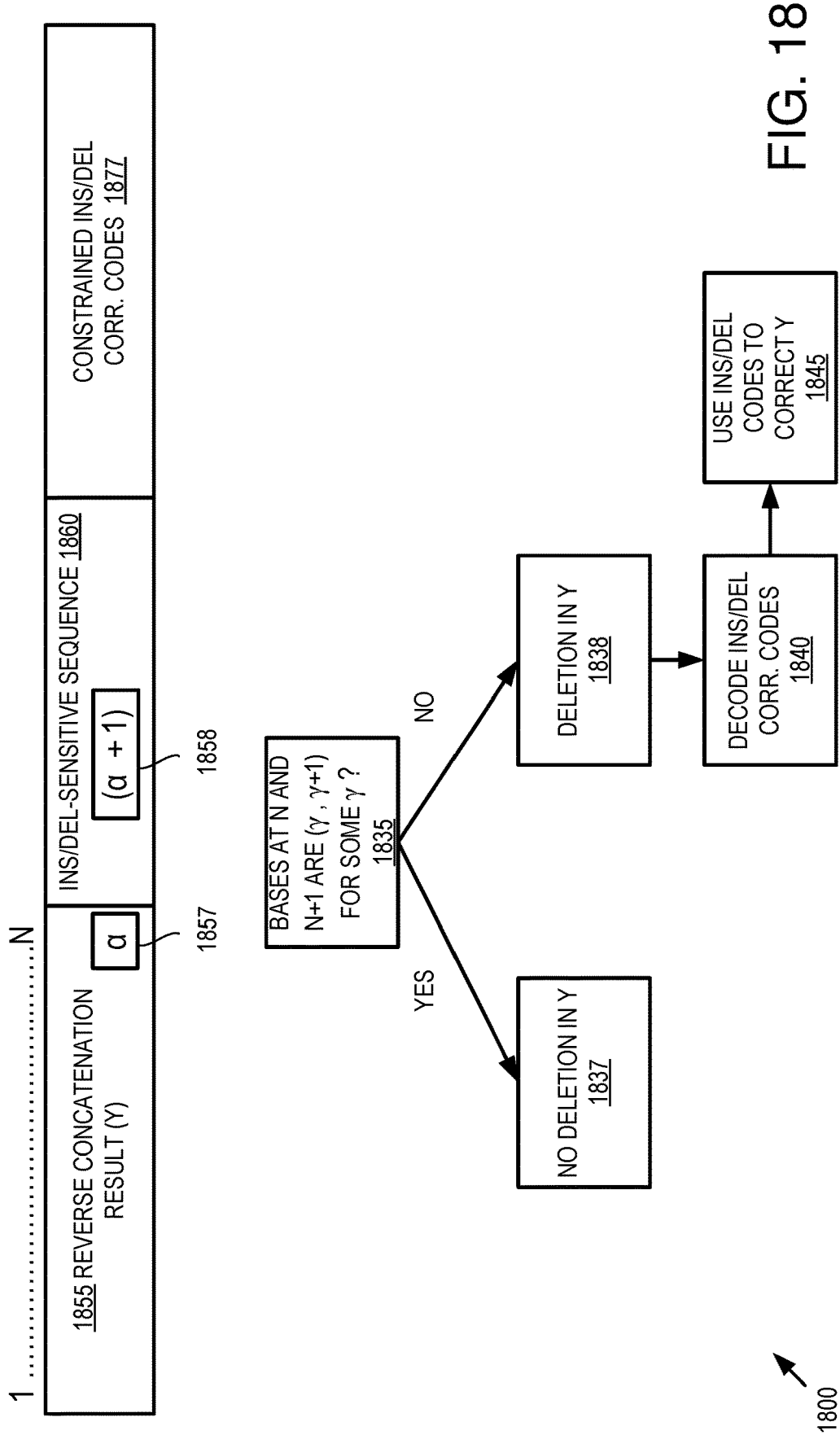
FIG. 18 is a block diagram of an example deletion case encountered when decoding a nucleotide symbol string incorporating insertion/deletion redundancy information.

FIG. 18 is a block diagram of an example deletion case 1800 encountered when decoding a nucleotide symbol string incorporating insertion/deletion redundancy information. If a symbol has been deleted (i.e., the length is one less than expected), a deletion case is indicated; however, it is still not known whether the deletion occurred in y or not.

As described herein, $\alpha$ 1857 and $(\alpha+1)$ 1858 have been chosen during encoding to be sequential. Therefore if the bases are observed to be sequential (e.g., the bases at n and n+1 are $(\gamma, \gamma+1)$ for some $\gamma$ using the modulo mapping above) at 1835, there is no deletion in y at 1837.

However, if not, there is a deletion in y at 1838. Accordingly, $H(C_{indel}(y))$ is believed to be free from errors and can be decoded at 1840. The resulting $C_{indel}(y)$ can then be used to correct the deletion error in y at 1845.

To summarize, it is determined whether consecutive symbols at an expected location of an insertion/deletion-sensitive sequence in one of the input nucleotide symbol strings exhibit sequential values. And if so, the deletion has not taken place within the main symbol string y of the input string.

Example 28—Example Insertion Case Detection

Figure 19:
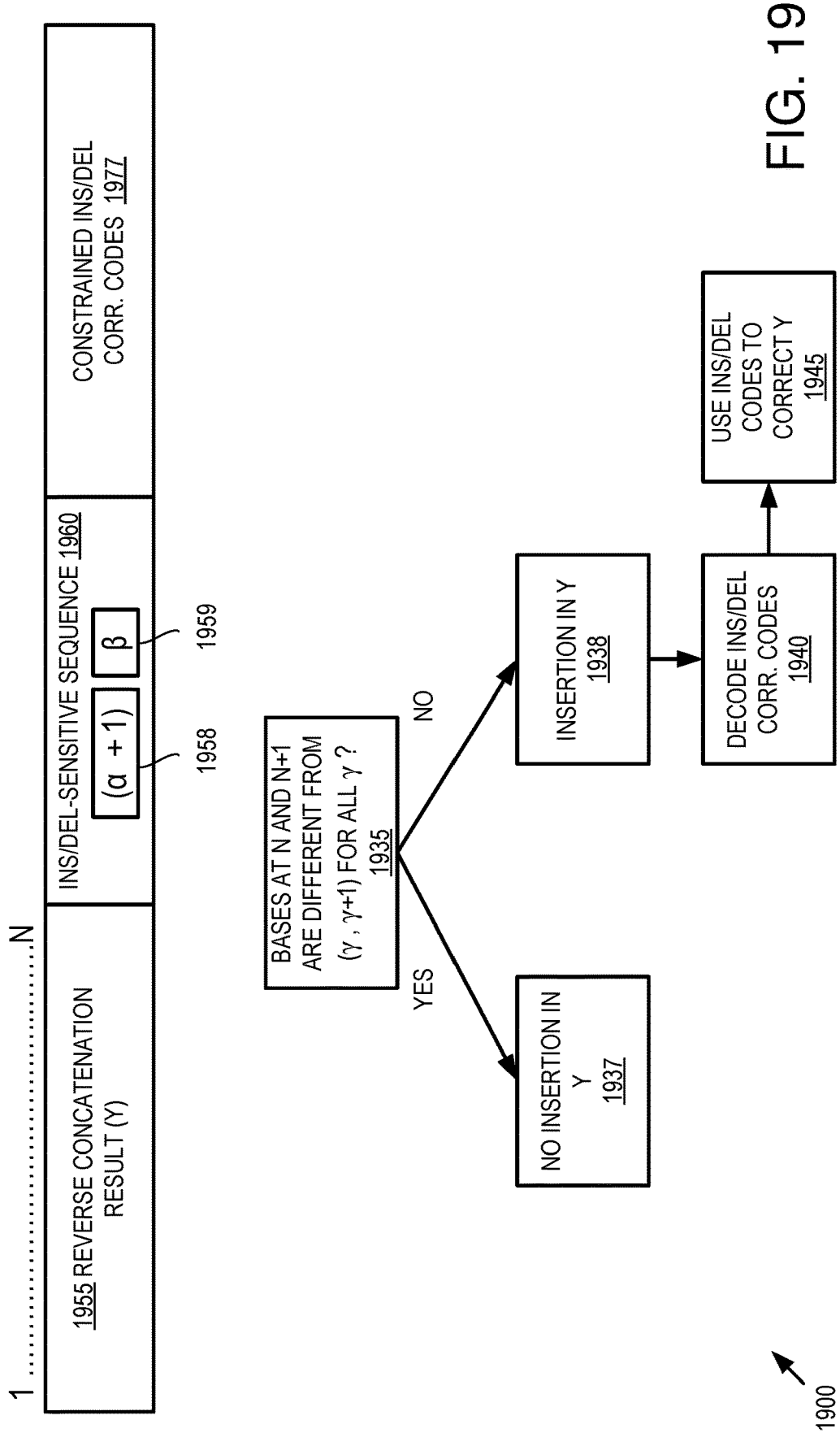
FIG. 19 is a block diagram of an example insertion case encountered when decoding a nucleotide symbol string incorporating insertion/deletion redundancy information.

FIG. 19 is a block diagram of an example insertion case 1900 encountered when decoding a nucleotide symbol string incorporating insertion/deletion redundancy information. If a symbol has been inserted (i.e., the length is one greater than expected), an insertion case is indicated; however, it is still not known whether the insertion occurred in y or not.

As described herein, $(\alpha+1)$ 1958 and $\beta$ 1959 have been chosen during encoding not to be sequential. Therefore if the bases are observed not to be sequential (e.g., the bases at n+1 and n+2 are different from (γ, γ+1) for all γ using the modulo mapping above) at 1935, there is no insertion in y at 1937.

However, if not, there is an insertion in y at 1938. Accordingly, $H(C_{indel}(y))$ is believed to be free from errors and can be decoded at 1940. The resulting $C_{indel}(y)$ can then be used to correct the insertion error in y at 1945. Because there is an insertion, the first n+1 bases of y' can be used during error correction.

To summarize, it is determined whether consecutive symbols at an expected location of an insertion/deletion-sensitive sequence in one of the input nucleotide symbol strings exhibit non-sequential values. And if so, the insertion has not taken place within the main symbol string y of the input string.

Example 29—Example Nucleotide Symbol String Data Structure

Figure 20:
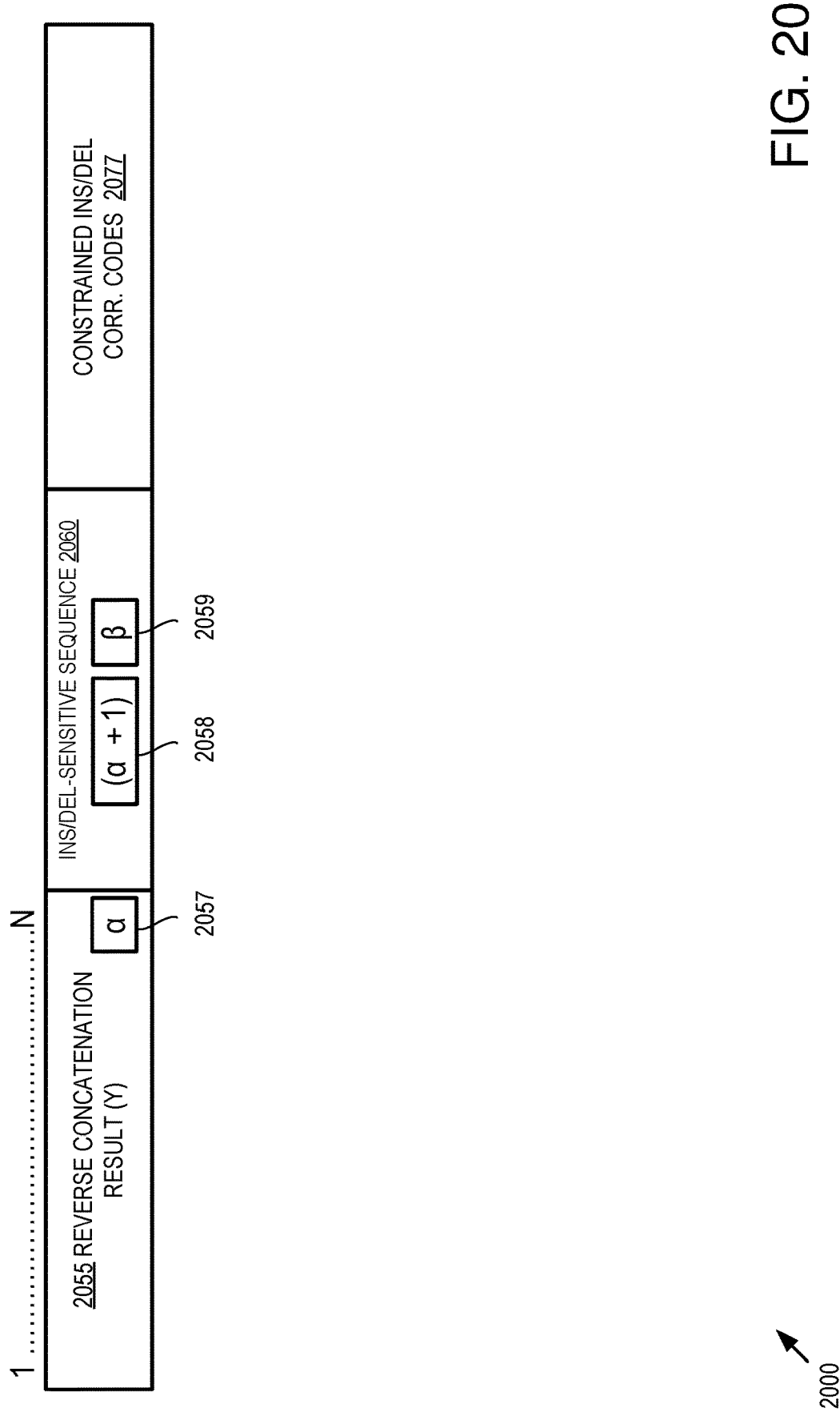
FIG. 20 is a block diagram of an example data structure suitable for representing data and redundancy information in a nucleotide symbol string.

FIG. 20 is a block diagram of an example data structure 2000 suitable for representing data and redundancy information in a nucleotide symbol string.

As described herein, the reverse concatenation result 2055 can be y (e.g., ending with α 2057) as described herein. The insertion/deletion-sensitive sequence 2060 can include (α+1) 2058 and β 2059 as described herein.

The constrained insertion/deletion correction code symbols 2077 can be $H(C_{indel}(y))$ as described herein.

The fields of the data structure 2000 are functionally related because the constrained insertion/deletion correction code symbols 2077 can be used to verify the integrity of and/or error correct the reverse concatenation result 2055. Further, the sequence 2060 can be used to detect whether an insertion/deletion occurs in the result 2055 or not during the decoding process, after errors have possibly been introduced into the structure 2000.

Therefore, the data structure 2000 is an error-resistant structure that accounts for insertion/deletion errors that can occur in the synthesis and/or sequencing processes.

Example 30—Example Decode System

Figure 21:
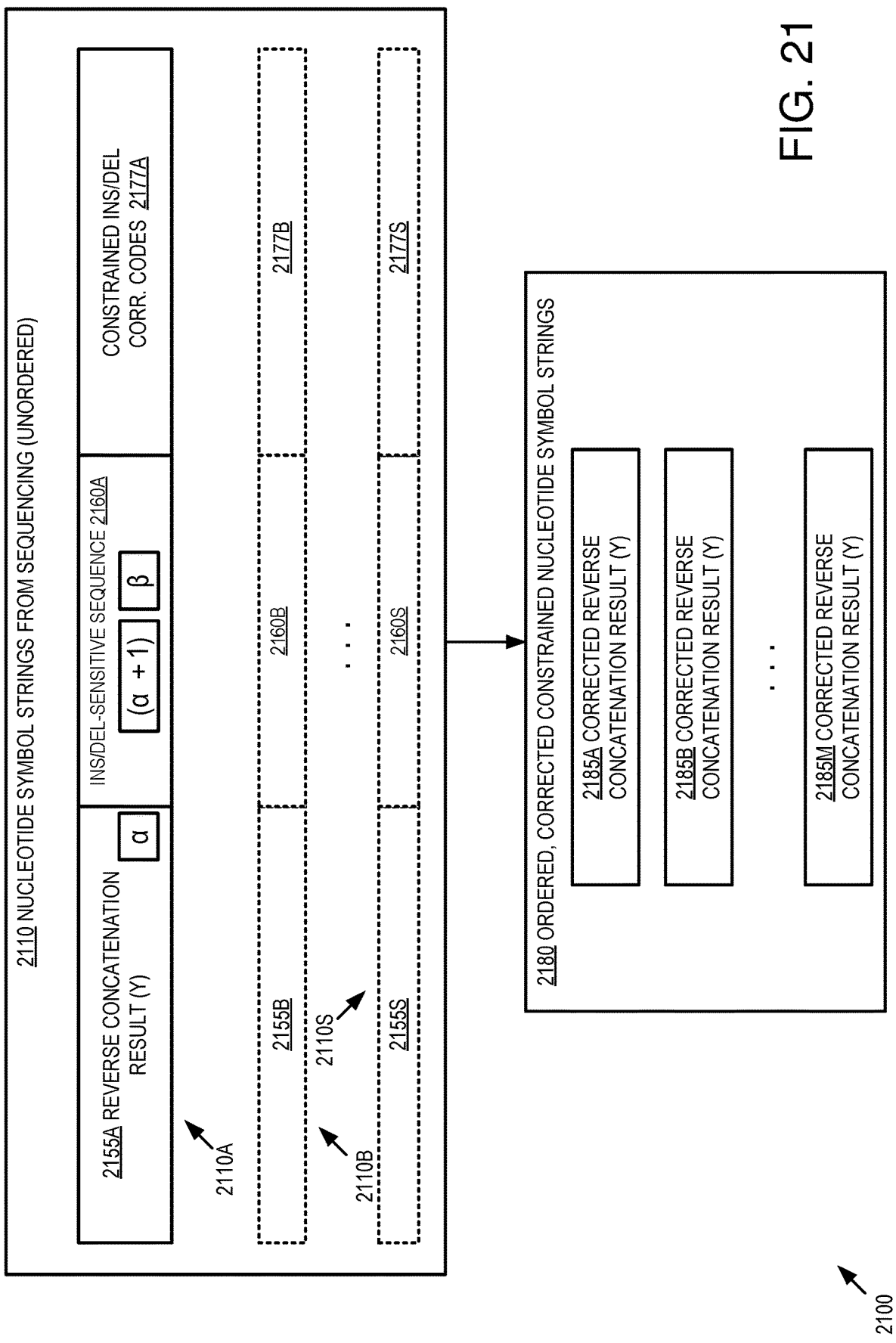
FIG. 21 is a block diagram of an example decoding system in a DNA data storage context.

FIG. 21 is a block diagram of an example decoding system in a DNA data storage context. In the example, a plurality of nucleotide symbol strings 2110A-S (e.g., a plurality of the structures shown in FIG. 20) have been sequenced from stored DNA data storage material (e.g., nucleotide strands). Although not shown, the strings can also include an address to assist in ordering. During storage, the strands are physically unordered, but are logically ordered by address. Decoding orders the strings 2110 resulting from sequencing by using the addresses stored thereon.

As described herein, the strings 2110 can include respective reverse concatenation results y 2155A-S, insertion/deletion-sensitive sequences 2160A-S, and constrained insertion/deletion correction codes 2177A-S (e.g., redundancy symbols for y).

As each of the strings 2110A-S are processed, they can be discarded or accepted based on their content and/or length. As a result, ordered, corrected constrained nucleotide symbol strings 2180 are assembled. In practice, a clustering algorithm can be used to resolve ambiguities for any differing strands that could be in the same position.

The ordered, corrected constrained nucleotide symbol strings 2180 can include a corrected reverse concatenation result y 2185A-M for each of the rows that were originally encoded. Inner and outer redundancy information can be interleaved therein as described herein. The resulting constrained representation can then be decoded to raw nucleotide symbol strings, which can then be converted to digital data representing the original file.

Example 31—Example Decode Implementation

Figure 22:
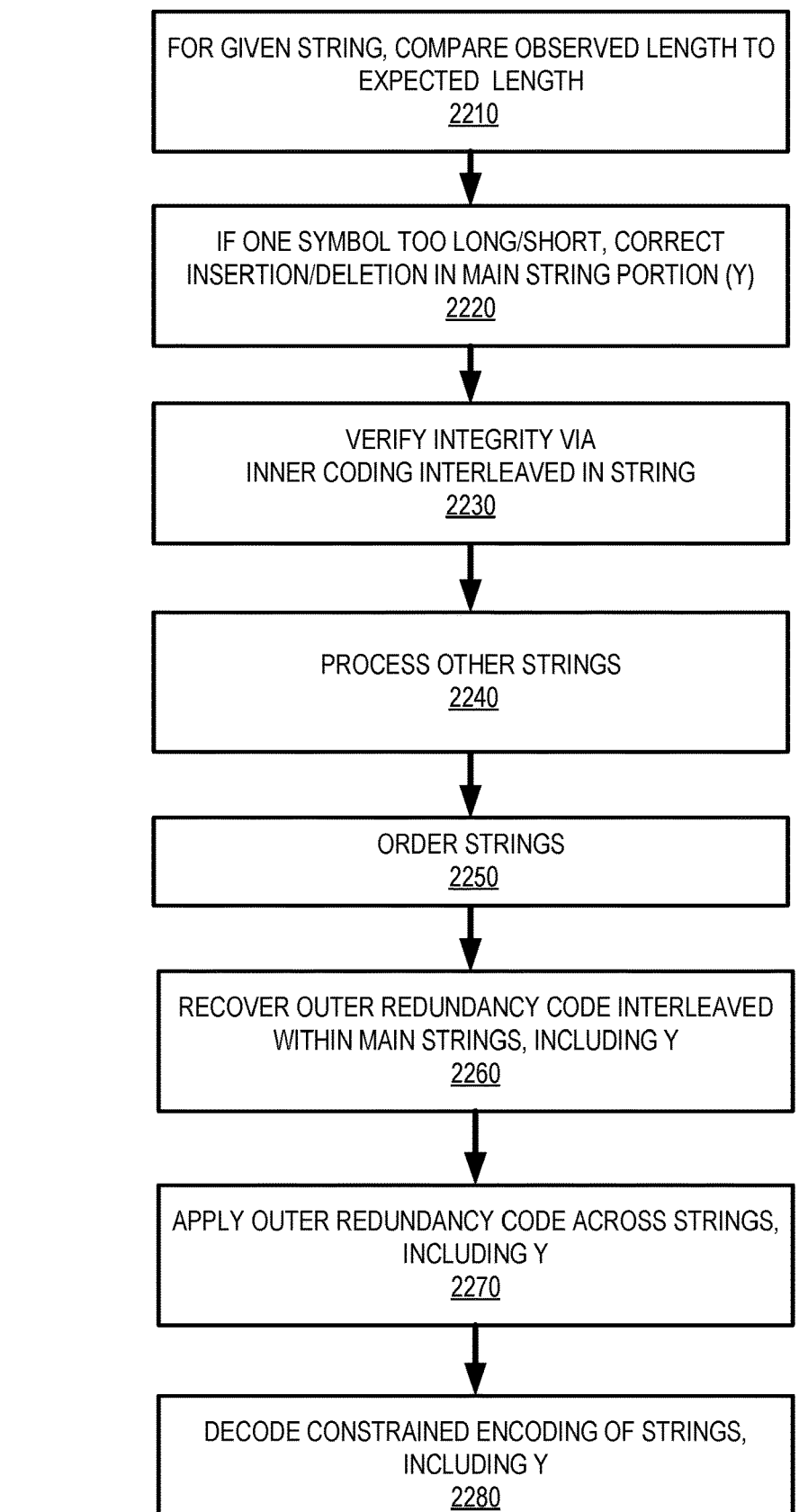
FIG. 22 is a flowchart of an example method of decoding nucleotide symbol strings incorporating reverse concatenation and including insertion/deletion redundancy information.

FIG. 22 is a flowchart of an example method 2200 of decoding nucleotide symbol strings incorporating reverse concatenation and including insertion/deletion redundancy information and can be implemented, for example, by a system such as that shown in FIG. 21. In the example, the method 2200 accepts a plurality of unordered strings that result from sequencing nucleotide strands that were encoded with encoding technologies described herein.

At 2210, for a given string out of the input nucleotide symbol strings, the observed length is compared with the expected length. Strings can be discarded as described herein.

At 2220, if the given string is exactly one symbol too long or too short, the main string portion (y) can be corrected using the redundancy information. For example, an insertion or deletion error can be corrected within a main symbol string portion (y) of the given input nucleotide symbol string via a redundancy coding extracted from the given input nucleotide symbol string.

At 2230, the integrity of the main string portion (y) is verified via a second (e.g., inner) redundancy code interleaved within the main symbol string (y). Such code can be extracted according to the how it was systematically interleaved within the string.

At 2240, other strings can be processed in a similar manner. However, the other different strings may have different scenarios (e.g., insertions, deletions, discarded, no errors, and the like).

At 2250, the strings are ordered (e.g., by an address field on the string).

At 2260, an outer redundancy code for substitutions that is interleaved in y's is recovered within the main portions of the ordered strings, including the main string portion (y) of the given string and.

At 2270 the outer redundancy code is applied across the main string portions (y's), including the main portion (y) of the given string (which has been corrected and verified), resulting in further corrected nucleotide symbol strings.

At 2280, the constrained encoding of the main portions (y) of the strings (including the given string) is decoded, resulting in the raw nucleotide symbol strings, which can then be decoded back to the original digital data.

Example 32—Example Advantages

The technologies herein can result in various advantages depending on implementation and context. For example, the ability to include redundancy information without subjecting it to a constrained encoding can lead to less propagation of error during the decoding process.

Fewer errors translate into a lower redundancy requirement, which then leads to a reduction in the amount of sequence coverage needed to decode a string, a reduction of the amount of redundancy symbols that need to be included in the encoded strings, and the like.

Because DNA synthesis and sequencing require time and materials (e.g., reagents), decreasing the coverage required or decreasing the number of redundancy symbols results in an overall lower cost, leading to more widespread availability of DNA data storage technologies in general.

Separately, a reduction in the number of errors by itself is also useful because it leads to more accurate and reliable DNA data storage technologies.

Further, during decoding, for redundancy information that does not have a constrained encoding applied to it, soft information (e.g., confidence information attached to individual bases that come from the DNA sequencer) can be passed directly to a decoder, often allowing for reduction in the overall redundancy of the coding scheme.

Example 33—Example Synthesis

Digital information that is intended for storage as DNA molecules can be converted into information representing a string of nucleotides (e.g., a nucleotide symbol string). The information representing the string of nucleotides (i.e., a string of letters representing an order of nucleotide bases) is used for DNA-synthesis templates that instruct an oligonucleotide synthesizer to chemically synthesize a DNA molecule, nucleotide by nucleotide. Artificial synthesis of DNA allows for creation of synthetic DNA molecules with arbitrary series of the bases in which individual monomers of the bases are assembled together into a polymer of nucleotides. The oligonucleotide synthesizer may be any oligonucleotide synthesizer using any recognized technique for DNA synthesis. The term "oligonucleotide" as used herein is defined as a molecule including two or more nucleotides.

The coupling efficiency of a synthesis process is the probability that a nucleotide binds to an existing partial strand at each step of the process. Although the coupling efficiency for each step can be higher than 99%, this small error still results in an exponential decrease of product yield with increasing length and limits the size of oligonucleotides that can be efficiently synthesized at present to about 200 nucleotides. Therefore, the length of the DNA strands put into storage is around 100 to 200 base pairs (bp). This length will increase with advances in oligonucleotide synthesis technology.

The synthetic DNA produced by the oligonucleotide synthesizer may be transferred to a DNA storage library. There are many possible ways to structure a DNA storage library. In addition to structure on the molecular level by appending identifying sequences to the DNA strands, a DNA storage library may be structured by physically separating DNA strands into one or more DNA pools. For illustration, a DNA pool is sometimes shown as a flip top tube representing a physical container for multiple DNA strands. DNA strands are generally most accessible for manipulation by bio-technological techniques when the DNA is stored in a liquid solution. Thus, the DNA pool can be implemented as a chamber filled with liquid, in many implementations water, and thousands, millions, or more individual DNA molecules may be present in a DNA pool.

Besides being in a liquid suspension, the DNA strands in the DNA storage library may be present in a glassy (or vitreous) state, as a lyophilized product, as part of a salt, adsorbed on the surface of a nanoparticle, or another format. The structure of the DNA pools may be implemented as any type of mechanical, biological, or chemical arrangement that holds a volume of liquid including DNA to a physical location. Storage may also be in a non-liquid form such as a solid bead or by encapsulation. For example, a single flat surface having a droplet present thereon, with the droplet held in part by surface tension of the liquid, even though not fully enclosed within a container, is one implementation of a DNA pool. The DNA pool may include single-stranded DNA (ssDNA), double-stranded DNA (dsDNA), single-stranded RNA (ssRNA), double-stranded RNA (dsRNA), DNA-RNA hybrid strands, or any combination, including use of unnatural bases.

Example 34—Example Sequencing

Stored nucleotide strands can be sequenced with a polynucleotide sequencer. In some implementations, DNA strands may be prepared for sequencing by amplification using polymerize chain reaction (PCR) to create a large number of DNA strands that are identical copies of each other. The need for PCR amplification prior to sequencing may depend on the specific sequencing technology used. PCR may itself be a source of error, although at a much lower level than current sequencing technology. At present, PCR techniques typically introduce one error per 10,000 bases. Thus, on average, for every 100 reads of 100 bases there will be one error that is the result of PCR. The errors introduced by PCR are generally distributed randomly so the trace reconstruction system will be able to correct some PCR-induced errors.

The polynucleotide sequencer reads the order of nucleotide bases in a DNA strand and generates one or more reads from that strand. Polynucleotide sequencers use a variety of techniques to interpret molecular information and may introduce errors into the data in both systematic and random ways. Errors can usually be categorized as substitution errors, where the real code is substituted with an incorrect code (for example A swapping with G), insertions, or deletions, where a random unit is inserted (for example AGT becoming AGCT) or deleted (for example AGTA becoming ATA). Each position in a read is an individual base call determined by the polynucleotide sequencer based on properties sensed by components of the polynucleotide sequencer. The various properties sensed by the polynucleotide sequencer vary depending on the specific sequencing technology used. A base call represents a determination of which of the four nucleotide bases—A, G, C, and T (or U)—in a strand of DNA (or RNA) is present at a given position in the strand. Sometimes the base calls are wrong and this is a source of error introduced by sequencing. Polynucleotide sequencing includes any method or technology that is used to generate base calls from a strand of DNA or RNA.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used is nanopore sequencing. A nanopore is a small hole of the order of 1 nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technology that can be used includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure that enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into an instrument, e.g., a HeliScope™ sequencer, and a laser illuminates the surface of the flow cell, revealing the position of each template. A CCD camera can map the position of the templates on the flow cell surface. The template fluorescent-label is then cleaved and washed away. The sequencing reaction begins by introducing a DNA polymerase and a fluorescently-labeled nucleotide. The oligo-T nucleic acid serves as a primer. The polymerase incorporates the labeled nucleotides to the primer in a template-directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently-labeled nucleotides until the desired read length is achieved. Sequence information is collected with each nucleotide addition step.

Another example of a DNA sequencing technique that can be used is SOLiD™ technology (Applied Biosystems). In SOLiD™ sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, templates, and PCR components. Following PCR, the templates are denatured and beads are enriched to separate the beads with extended templates. Templates on the selected beads are subjected to a 3' modification that permits bonding to a glass slide.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

Technologies for sequencing DNA are associated with some level of error and the type and frequency of errors differs by sequencing technology. For example, sequencing-by-synthesis creates an error in about 2% of the base calls. A majority of these errors are substitution errors. Nanopore sequencing has a much higher error rate of about 15 to 40% and most of the errors caused by this sequencing technology are deletions. The error profile of a specific sequencing technology may describe the overall frequency of errors as well as the relative frequency of various types of errors.

In some implementations, the polynucleotide sequencer provides quality information that indicates a level of confidence in the accuracy of a given base call. The quality information may indicate that there is a high level or a low level of confidence in a particular base call. For example, the quality information may be represented as a percentage, such as 80% confidence, in the accuracy of a base call. Additionally, quality information may be represented as a level of confidence that each of the four bases is the correct base call for a given position in a DNA strand. For example, quality information may indicate that there is 80% confidence the base call is a T, 18% confidence the base call is an A, 1% confidence the base call is a G, and 1% confidence the base call is a C. Thus, the result of this base call would be T because there is higher confidence in that nucleotide being the correct base call than in any of the other nucleotides. Quality information does not identify the source of an error, but merely suggests which base calls are more or less likely to be accurate.

The polynucleotide sequencer provides output, multiple noisy reads (possibly of multiple DNA strands), in electronic format to a trace reconstruction system. The output may include the quality information as metadata for otherwise associated with the reads produced by the polynucleotide sequencer.

The trace reconstruction system can be implemented as an integral part of the polynucleotide sequencer. The polynucleotide sequencer can include an onboard computer that implements the trace reconstruction system. Alternatively, the trace reconstruction system may be implemented as part of a separate computing device that is connected to the polynucleotide sequencer through a wired or wireless connection. For example, the computing device may be a desktop or notebook computer used to receive data from and/or to control the polynucleotide sequencer. A wired connection may include one or more wires or cables physically connecting the computing device to the polynucleotide sequencer. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. The trace reconstruction system may also be implemented as part of a cloud-based or network system using one or more servers that communicate with the polynucleotide sequencer via a network. The network may be implemented as any type of communications network such as a local area network, a wide area network, a mesh network, an ad hoc network, a peer-to-peer network, the Internet, a cable network, a telephone network, and the like. Additionally, the trace reconstruction system may be implemented in part by any combination of the polynucleotide sequencer, the computing device, and the servers.

The trace reconstruction system outputs a digital representation of the result strands for further processing as described herein. In practice, the results of integrity checking can be incorporated into the trace reconstruction process if desired.

Example 35—Example Computing Systems

Figure 23:
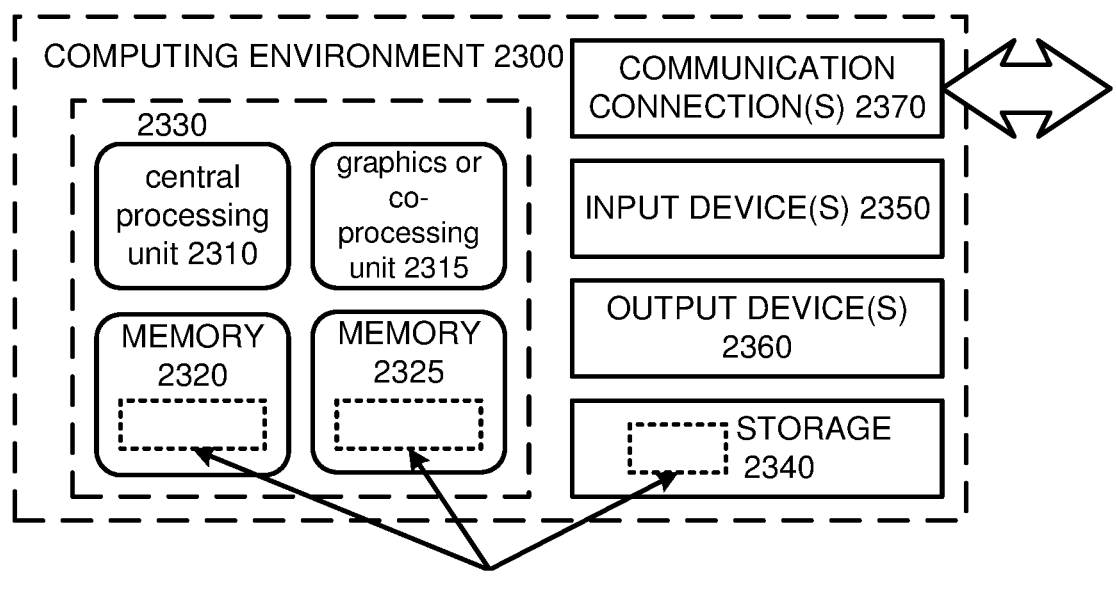
FIG. 23 is a block diagram of an example computing system in which described embodiments can be implemented.

FIG. 23 depicts an example of a suitable computing system 2300 in which digital aspects of the described innovations can be implemented. The computing system 2300 is not intended to suggest any limitation as to scope of use or functionality of the present disclosure, as the innovations can be implemented in diverse computing systems.

With reference to FIG. 23, the computing system 2300 includes one or more processing units 2310, 2315 and memory 2320, 2325. In FIG. 23, this basic configuration 2330 is included within a dashed line. The processing units 2310, 2315 execute computer-executable instructions, such as for implementing the features described in the examples herein. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 23 shows a central processing unit 2310 as well as a graphics processing unit or co-processing unit 2315. The tangible memory 2320, 2325 can be volatile memory (e.g., registers, cache, RAM), non-volatile memory (e.g., ROM, EEPROM, flash memory, etc.), or some combination of the two, accessible by the processing unit(s) 2310, 2315. The memory 2320, 2325 stores software 2380 implementing one or more innovations described herein, in the form of computer-executable instructions suitable for execution by the processing unit(s) 2310, 2315.

Functionality can also be performed, at least in part, by one or more hardware logic components. For example, Field-programmable Gate Arrays (FPGAs), Application-specific Standard Products (ASSPs), System-on-a chip systems (SOCs), Complex Programmable Logic Devices (CPLDs), and the like can be used.

A computing system 2300 can have additional features. For example, the computing system 2300 includes storage 2340, one or more input devices 2350, one or more output devices 2360, and one or more communication connections 2370, including input devices, output devices, and communication connections for interacting with a user. An interconnection mechanism (not shown) such as a bus, controller, or network interconnects the components of the computing system 2300. Typically, operating system software (not shown) provides an operating environment for other software executing in the computing system 2300, and coordinates activities of the components of the computing system 2300.

The tangible storage 2340 can be removable or non-removable, and includes magnetic disks, magnetic tapes or cassettes, CD-ROMs, DVDs, or any other medium which can be used to store information in a non-transitory way and which can be accessed within the computing system 2300. The storage 2340 stores instructions for the software 2380 implementing one or more innovations described herein.

The input device(s) 2350 can be an input device such as a keyboard, mouse, pen, or trackball, a voice input device, a scanning device, touch device (e.g., touchpad, display, or the like) or another device that provides input to the computing system 2300. The output device(s) 2360 can be a display, printer, speaker, CD-writer, or another device that provides output from the computing system 2300.

The communication connection(s) 2370 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Example 36—Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example 37—Example Cloud Computing Environment

Figure 24:
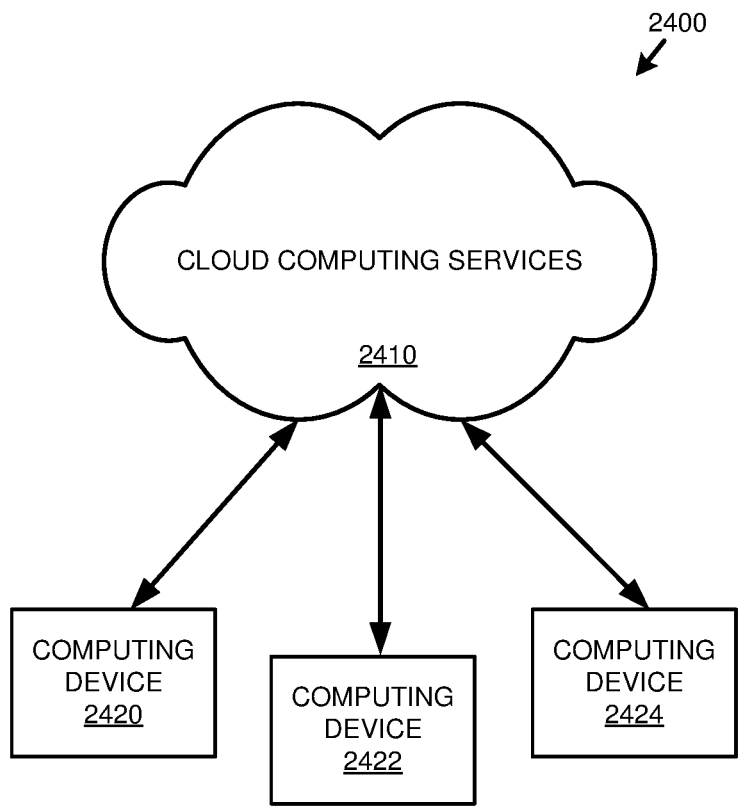
FIG. 24 is a block diagram of an example cloud computing environment that can be used in conjunction with the technologies described herein.

FIG. 24 depicts an example cloud computing environment 2400 in which the described technologies can be implemented, including, e.g., the system 100 of FIG. 1 and other systems herein. The cloud computing environment 2400 comprises cloud computing services 2410. The cloud computing services 2410 can comprise various types of cloud computing resources, such as computer servers, data storage repositories, networking resources, etc. The cloud computing services 2410 can be centrally located (e.g., provided by a data center of a business or organization) or distributed (e.g., provided by various computing resources located at different locations, such as different data centers and/or located in different cities or countries).

The cloud computing services 2410 are utilized by various types of computing devices (e.g., client computing devices), such as computing devices 2420, 2422, and 2424. For example, the computing devices (e.g., 2420, 2422, and 2424) can be computers (e.g., desktop or laptop computers), mobile devices (e.g., tablet computers or smart phones), or other types of computing devices. For example, the computing devices (e.g., 2420, 2422, and 2424) can utilize the cloud computing services 2410 to perform computing operations (e.g., data processing, data storage, and the like).

In practice, cloud-based, on-premises-based, or hybrid scenarios can be supported.

Example 38—Example Implementations

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Example 39—Example Embodiments

Any of the following embodiments can be implemented.
Clause 1. A method comprising:
for input nucleotide symbol strings representing input data to be encoded as nucleotides, converting the input nucleotide symbol strings to constrained nucleotide symbol strings completely representing the input nucleotide symbol strings and satisfying a coding constraint;
after converting the input nucleotide symbol strings to the constrained nucleotide symbol strings, calculating a redundancy code for the constrained nucleotide symbol strings, wherein the redundancy code carries redundancy information for the constrained nucleotide symbol strings and comprises a plurality of redundancy code nucleotide symbols; and
incorporating the redundancy code nucleotide symbols of the redundancy code and the constrained nucleotide symbol strings into result nucleotide symbol strings, wherein the result strings satisfy a relaxed version of the coding constraint, completely represent the input nucleotide symbol strings, and comprise the redundancy information for the constrained nucleotide symbol strings.

Clause 2. The method of Clause 1 wherein:
the coding constraint comprises limiting homopolymer runs to n consecutive instances; and
the relaxed version of the coding constraint comprises limiting homopolymer runs to n+1 consecutive instances;
wherein n is an integer greater than 0.

Clause 3. The method of any of Clauses 1-2 wherein:
incorporating the redundancy code nucleotide symbols comprises interleaving the redundancy code nucleotide symbols into the constrained nucleotide symbol strings.

Clause 4. The method of any of Clauses 1-3 wherein:
incorporating the redundancy code nucleotide symbols comprises placing the redundancy code nucleotide symbols in reserved nucleotide symbol spaces interleaved within the constrained nucleotide symbol strings.

Clause 5. The method of Clause 4 further comprising:
systematically calculating regularly recurring positions for the reserved nucleotide symbol spaces.

Clause 6. The method of an of Clauses 4-5 wherein:
at least one of the reserved nucleotide symbol spaces has a size of greater than one symbol.

Clause 7. The method of any of Clauses 1-6 wherein:
calculating the redundancy code comprises calculating an outer redundancy code across the constrained nucleotide symbol strings.

Clause 8. The method of Clause 7 wherein:
the outer redundancy code is configured to correct a substitution error within nucleotide symbols across the constrained nucleotide symbol strings.

Clause 9. The method of any of Clauses 1-8 wherein:
calculating the redundancy code comprises calculating an inner redundancy code within the constrained nucleotide symbol strings.

Clause 10. The method of any of Clauses 1-9 wherein:
calculating the redundancy code comprises:
calculating an outer redundancy code across the constrained nucleotide symbol strings; and
calculating an inner redundancy code within the constrained nucleotide symbol strings.

Clause 11. The method of Clause 10 wherein:
the inner redundancy code is configured to correct substitution errors within the constrained nucleotide symbol strings.

Clause 12. The method of Clause 11 further comprising:
calculating insertion/deletion correction codes for the result nucleotide symbol strings;
encoding the insertion/deletion correction codes with a constrained mapping, yielding constrained insertion/deletion correction codes;
calculating insertion/deletion-sensitive sequences for the result nucleotide symbol strings; and
incorporating the constrained insertion/deletion correction codes and the insertion/deletion-sensitive sequences into the result nucleotide symbol strings.

Clause 13. One or more computer-readable media having encoded thereon computer-executable instructions that when executed cause a computing system to perform the method of any of Clauses 1-12.

Clause 14. A method comprising:
for input nucleotide symbol strings representing sequencing data to be decoded as output digital data, recovering a plurality of redundancy code nucleotide symbols carrying redundancy information and systematically interleaved throughout the input nucleotide symbol strings;
for the input nucleotide symbol strings representing sequencing input data to be decoded as output digital data, recovering a plurality of underlying nucleotide symbol strings;
applying the redundancy information of the redundancy code nucleotide symbols to the underlying nucleotide symbol strings, wherein the applying results in correction or verification of the underlying nucleotide symbol strings.

Clause 15. The method of Clause 14 wherein:
the input nucleotide symbol strings comprise respective addresses indicating an order of the input nucleotide symbol strings.

Clause 16. The method of Clause 15 further comprising:
ordering the underlying nucleotide symbol strings according to the respective addresses of the strings.

Clause 17. The method of any of Clauses 14-16 wherein:
the redundancy code nucleotide symbols comprise an outer encoding configured to correct a substitution error within nucleotide symbols across the underlying nucleotide symbol strings.

Clause 18. The method of any of Clauses 14-17 wherein:
an encoding to satisfy a coding constraint has been applied to the underlying nucleotide symbol strings; but
the encoding to satisfy the coding constraint has not been applied to the plurality of redundancy code nucleotide symbols.

Clause 19. The method of any of Clauses 14-18 further comprising:
at an expected location of an insertion/deletion-sensitive sequence in one of the input nucleotide symbol strings, determining whether consecutive symbols exhibit sequential values; and
based on whether the consecutive symbols exhibit sequential values, determining whether a deletion has taken place within a main symbol string.

Clause 20. The method of any of Clauses 14-19 further comprising:
at an expected location of an insertion/deletion-sensitive sequence in one of the input nucleotide symbol strings, determining whether consecutive symbols exhibit non-sequential values; and
based on whether the consecutive symbols exhibit non-sequential values, determining whether an insertion has taken place within a main symbol string.

Clause 21. One or more computer-readable media having encoded thereon computer-executable instructions that when executed cause a computing system to perform the method of any of Clauses 14-20.

Clause 22. One or more computer-readable media comprising:
computer-executable instructions capable of causing a computing system to receive a plurality of input nucleotide symbol strings representing underlying data;
computer-executable instructions capable of causing the computing system to, for a given input nucleotide symbol string out of the input nucleotide symbol strings, compare an observed length to an expected length;
computer-executable instructions capable of causing the computing system to, responsive to determining that the given input nucleotide symbol string is exactly one symbol too long or short, correcting an insertion or deletion error within a main symbol string portion of the given input nucleotide symbol string via a redundancy coding extracted from the given input nucleotide symbol string;
computer-executable instructions capable of causing the computing system to verify integrity of the corrected main symbol string portion of the given string via a second redundancy code interleaved within the main symbol string portion of the given string; and
computer-executable instructions capable of causing the computing system to recover outer coding redundancy information interleaved across main portions of nucleotide symbol strings comprising the corrected, verified main portion of the given string;
applying the outer coding redundancy information across the main portions of the nucleotide symbol strings, resulting in further corrected nucleotide symbol strings; and
decoding a constrained encoding of the further corrected nucleotide symbol strings.

Example 40—Example Alternatives

The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the following claims.

What is claimed is:
1. A method comprising:
by a computing system, for input nucleotide symbol strings representing input data to be encoded as nucleotides, converting the input nucleotide symbol strings to constrained nucleotide symbol strings completely representing the input nucleotide symbol strings and satisfying a consecutive homopolymer coding constraint that comprises limiting homopolymer runs to n consecutive instances, wherein n is an integer greater than 0;
by the computing system, after converting the input nucleotide symbol strings to the constrained nucleotide symbol strings, calculating a redundancy code for the constrained nucleotide symbol strings, wherein the redundancy code carries redundancy information for the constrained nucleotide symbol strings and comprises a plurality of redundancy code nucleotide symbols;
by the computing system, incorporating the redundancy code nucleotide symbols of the redundancy code and the constrained nucleotide symbol strings into result nucleotide symbol strings, wherein the result strings satisfy a relaxed version of the consecutive homopolymer coding constraint, completely represent the input nucleotide symbol strings, and comprise the redundancy information for the constrained nucleotide symbol strings, wherein incorporating the redundancy code nucleotide symbols comprises interleaving the redundancy code nucleotide symbols into the constrained nucleotide symbol strings while satisfying the relaxed version of the consecutive homopolymer coding constraint;

instructing an oligonucleotide synthesizer to chemically synthesize DNA molecules according to the result nucleotide symbol strings; and synthesizing a plurality of nucleotide strands according to the result nucleotide symbol strings, wherein the nucleotide strands satisfy the relaxed version of the consecutive homopolymer constraint and represent redundancy code nucleotide symbols calculated after converting the input converting the input nucleotide symbol strings to the constrained nucleotide symbol strings.

2. The method of claim 1 wherein:
the relaxed version of the coding constraint comprises limiting homopolymer runs to n+1 consecutive instances.

3. The method of claim 1 wherein:
incorporating the redundancy code nucleotide symbols comprises placing the redundancy code nucleotide symbols in reserved nucleotide symbol spaces interleaved within the constrained nucleotide symbol strings.

4. The method of claim 3 further comprising:
systematically calculating regularly recurring positions for the reserved nucleotide symbol spaces.

5. The method of claim 3 wherein:
at least one of the reserved nucleotide symbol spaces has a size of greater than one symbol.

6. The method of claim 1 wherein:
calculating the redundancy code comprises calculating an outer redundancy code across the constrained nucleotide symbol strings.

7. The method of claim 6 wherein:
the outer redundancy code is configured to correct a substitution error within nucleotide symbols across the constrained nucleotide symbol strings.

8. The method of claim 1 wherein:
calculating the redundancy code comprises calculating an inner redundancy code within the constrained nucleotide symbol strings.

9. The method of claim 1 wherein:
calculating the redundancy code comprises:
calculating an outer redundancy code across the constrained nucleotide symbol strings; and
calculating an inner redundancy code within the constrained nucleotide symbol strings.

10. The method of claim 9 wherein:
the inner redundancy code is configured to correct substitution errors within the constrained nucleotide symbol strings.

11. The method of claim 10 further comprising:
calculating insertion/deletion correction codes for the result nucleotide symbol strings;
encoding the insertion/deletion correction codes with a constrained mapping, yielding constrained insertion/deletion correction codes;
calculating insertion/deletion-sensitive sequences for the result nucleotide symbol strings; and incorporating the constrained insertion/deletion correction codes and the insertion/deletion-sensitive sequences into the result nucleotide symbol strings.

12. The method of claim 11 wherein:
calculating the insertion/deletion-sensitive sequences comprises employing a nucleotide modulo function.

13. A method comprising:
receiving a plurality of synthesized nucleotide strands, wherein the nucleotide strands encode a plurality of underlying nucleotide strings and are encoded as nucleotides via (a)-(e):

(a) by a computing system, for input nucleotide symbol strings representing input data to be encoded as nucleotides, converting the input nucleotide symbol strings to constrained nucleotide symbol strings completely representing the input nucleotide symbol strings and satisfying a consecutive homopolymer coding constraint that comprises limiting homopolymer runs to n consecutive instances, wherein n is an integer greater than 0;

(b) by the computing system, after converting the input nucleotide symbol strings to the constrained nucleotide symbol strings, calculating a redundancy code for the constrained nucleotide symbol strings, wherein the redundancy code carries redundancy information for the constrained nucleotide symbol strings and comprises a plurality of redundancy code nucleotide symbols;

(c) by the computing system, incorporating the redundancy code nucleotide symbols of the redundancy code and the constrained nucleotide symbol strings into result nucleotide symbol strings, wherein the result strings satisfy a relaxed version of the consecutive homopolymer coding constraint, completely represent the input nucleotide symbol strings, and comprise the redundancy information for the constrained nucleotide symbol strings, wherein incorporating the redundancy code nucleotide symbols comprises interleaving the redundancy code nucleotide symbols into the constrained nucleotide symbol strings while satisfying the relaxed version of the consecutive homopolymer coding constraint;

(d) instructing an oligonucleotide synthesizer to chemically synthesize DNA molecules according to the result nucleotide symbol strings; and (e) synthesizing the plurality of nucleotide strands according to the result nucleotide symbol strings, wherein the nucleotide strands satisfy the relaxed version of the consecutive homopolymer constraint and represent redundancy code nucleotide symbols calculated after converting the input converting the input nucleotide symbol strings to the constrained nucleotide symbol strings;

sequencing the plurality of nucleotide strands, wherein the sequencing outputs input nucleotide symbol strings representing sequencing data to be decoded as output digital data;

by a computing system, for the input nucleotide symbol strings representing sequencing data to be decoded as output digital data, recovering a plurality of redundancy code nucleotide symbols carrying redundancy information and systematically interleaved throughout the input nucleotide symbol strings, wherein the input nucleotide symbol strings satisfy a relaxed version of a consecutive homopolymer coding constraint;

by the computing system, for the input nucleotide symbol strings representing sequencing input data to be decoded as output digital data, recovering the plurality of underlying nucleotide symbol strings; and by the computing system, applying the redundancy information of the redundancy code nucleotide symbols to the underlying nucleotide symbol strings, wherein the applying results in correction or verification of the underlying nucleotide symbol strings.

14. The method of claim 13 wherein:

the input nucleotide symbol strings representing sequencing data to be decoded as output digital data comprise respective addresses indicating an order of the input nucleotide symbol strings.

15. The method of claim 14 further comprising:

ordering the underlying nucleotide symbol strings according to the respective addresses of the strings.

16. The method of claim 13 wherein:

the redundancy code nucleotide symbols comprise an outer encoding configured to correct a substitution error within nucleotide symbols across the underlying nucleotide symbol strings.

17. The method of claim 13 wherein:

an encoding to satisfy a coding constraint has been applied to the underlying nucleotide symbol strings; but the encoding to satisfy the coding constraint has not been applied to the plurality of redundancy code nucleotide symbols.

18. The method of claim 13 further comprising:

at an expected location of an insertion/deletion-sensitive sequence in one of the input nucleotide symbol strings representing sequencing data to be decoded as output digital data, determining whether consecutive symbols exhibit sequential values; and based on whether the consecutive symbols exhibit sequential values, determining whether a deletion has taken place within a main symbol string.

19. The method of claim 13 further comprising:

at an expected location of an insertion/deletion-sensitive sequence in one of the input nucleotide symbol strings, determining whether consecutive symbols exhibit non-sequential values; and based on whether the consecutive symbols exhibit non-sequential values, determining whether an insertion has taken place within a main symbol string.

* * * * *